United States Patent
Dale et al.

(10) Patent No.: US 10,334,856 B2
(45) Date of Patent: *Jul. 2, 2019

(54) NON-TOXIC PEST CONTROL COMPOSITIONS AND METHODS AND USES THEREOF

(71) Applicant: Neozyme International, Inc., Costa Mesa, CA (US)

(72) Inventors: Parker Dale, Newport Beach, CA (US); Parker David Dale, Newport Beach, CA (US)

(73) Assignee: Neozyme International, Inc., Costa Mesa, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/243,957

(22) Filed: Aug. 22, 2016

(65) Prior Publication Data

US 2016/0360758 A1   Dec. 15, 2016

Related U.S. Application Data

(63) Continuation-in-part of application No. 14/404,917, filed as application No. PCT/US2013/000140 on May 24, 2013, now Pat. No. 9,617,178.

(60) Provisional application No. 61/689,077, filed on May 29, 2012, provisional application No. 62/208,662, filed on Aug. 22, 2015.

(51) Int. Cl.
*A01N 63/02* (2006.01)
*A01N 63/04* (2006.01)

(52) U.S. Cl.
CPC ............. *A01N 63/02* (2013.01); *A01N 63/04* (2013.01)

(58) Field of Classification Search
CPC .......... A01N 63/04; A01N 63/02; A01N 63/00
See application file for complete search history.

(56) References Cited

U.S. PATENT DOCUMENTS

| | | |
|---|---|---|
| 3,635,797 A | 1/1972 | Battistoni et al. |
| 4,052,858 A | 10/1977 | Jeppson et al. |
| 4,541,986 A | 9/1985 | Schwab et al. |
| 4,666,606 A | 5/1987 | Heinicke |
| 4,758,353 A | 7/1988 | Spence et al. |
| 4,804,478 A | 2/1989 | Tamir |
| 5,071,765 A | 12/1991 | Wiatr |
| 5,075,008 A | 12/1991 | Chigusa et al. |
| 5,139,945 A | 8/1992 | Liu |
| 5,179,003 A | 1/1993 | Wolf et al. |
| 5,227,067 A | 7/1993 | Runyon |
| 5,284,844 A | 2/1994 | Lorenz et al. |
| 5,326,477 A | 7/1994 | Fugua et al. |
| 5,369,031 A | 11/1994 | Middleditch et al. |
| 5,407,577 A | 4/1995 | Nghiem |
| 5,462,868 A | 10/1995 | Britt et al. |
| 5,500,306 A | 3/1996 | Hsu et al. |
| 5,736,209 A | 4/1998 | Andersen et al. |
| 5,820,758 A | 12/1998 | Dale et al. |
| 5,849,566 A | 12/1998 | Dale et al. |
| 5,866,376 A * | 2/1999 | Rocha ............... C07H 15/04 435/100 |
| 5,879,928 A | 3/1999 | Dale et al. |
| 5,885,590 A | 3/1999 | Hunter et al. |
| 5,885,950 A | 3/1999 | Dale et al. |
| 6,699,391 B2 | 3/2004 | Baldridge et al. |
| 6,783,679 B1 | 8/2004 | Rozich |
| 6,841,572 B2 * | 1/2005 | Horst ............... A01N 37/06 514/557 |
| 6,884,351 B1 | 4/2005 | Lytal |
| 7,165,561 B2 | 1/2007 | Baldridge et al. |
| 7,476,529 B2 | 1/2009 | Podella et al. |
| 7,645,730 B2 | 1/2010 | Baldridge et al. |
| 7,658,848 B2 | 2/2010 | Baldridge et al. |
| 7,659,237 B2 | 2/2010 | Baldridge et al. |
| 7,759,301 B2 | 7/2010 | Baldridge et al. |
| 7,922,906 B2 | 4/2011 | Baldridge et al. |
| 8,188,028 B2 | 5/2012 | Baldridge et al. |
| 8,389,459 B2 | 3/2013 | Baldridge et al. |
| 8,735,338 B2 | 5/2014 | Baldridge et al. |
| 8,835,152 B2 | 9/2014 | Podella |
| 8,871,682 B2 | 10/2014 | Michalow et al. |
| 8,871,698 B2 | 10/2014 | Podella et al. |
| 8,894,861 B2 | 11/2014 | Podella et al. |
| 9,051,535 B2 | 6/2015 | Goldfeld et al. |
| 9,617,178 B2 | 4/2017 | Dale et al. |

(Continued)

FOREIGN PATENT DOCUMENTS

CN    101557249 A    10/2009
CN    101951686 A    1/2011

(Continued)

OTHER PUBLICATIONS

Desai, JD et al. Microbial production of surfactants and their commercial potential. Microbiology and Molecular Biology Reviews. Mar. 1997. 61(1): 47-64. (Year: 1997).*
Witek-Krowiak, A et al. Ultrafiltrative separation of rhamnolipid from culture medium. World J. Microbiol. Biotechnol. 2011. 27: 1961-1964. Published online Jan. 19, 2011. (Year: 2011).*
Xu, Q et al. Biosurfactants for microbubble preparation and application. Int. J. Mol. Sci. 2011. 12: 462-475. (Year: 2011).*
International Search Report PCT/US2013/000140, dated Jul. 22, 2013.
Ku, Kai-Yu, et al., "Research Review of Wastewater Treatment Technology with Hydrolytic Enzymes," vol. 12, No. 6, Journal of Chongqing University of Science and technology, Natural Sciences Edition (Dec. 2010).

(Continued)

*Primary Examiner* — Renee Claytor
*Assistant Examiner* — Susan E. Fernandez
(74) *Attorney, Agent, or Firm* — UltimatEdge IP Law Group, P.C.; Dean G. Stathakis

(57) ABSTRACT

The present specification discloses pest control compositions, articles of manufacture, containers or kits comprising such compositions, and methods and uses to control a population of invertebrate pests from a mammal, location, plant, structure treated of such pest control compositions.

19 Claims, No Drawings

(56) References Cited

U.S. PATENT DOCUMENTS

| | | |
|---|---|---|
| 2003/0121868 A1 | 7/2003 | Barak et al. |
| 2004/0180411 A1 | 9/2004 | Podella et al. |
| 2005/0164355 A1 | 7/2005 | Vlasenko et al. |
| 2005/0171275 A1 | 8/2005 | De Jong et al. |
| 2005/0266036 A1 | 12/2005 | Awada et al. |
| 2006/0205042 A1 | 9/2006 | Aehle et al. |
| 2007/0029264 A1 | 2/2007 | Bowe |
| 2007/0224249 A1 | 9/2007 | Kelly et al. |
| 2008/0138327 A1 | 6/2008 | Kelly |
| 2009/0152196 A1 | 6/2009 | Podella |
| 2010/0078307 A1 | 4/2010 | Dale et al. |
| 2010/0273495 A1 | 10/2010 | Onggosanusi et al. |
| 2011/0052514 A1 | 3/2011 | Justen |
| 2012/0100236 A1* | 4/2012 | Asolkar ............... A01N 43/90 424/780 |
| 2012/0172219 A1 | 7/2012 | Podella et al. |
| 2013/0104264 A1 | 4/2013 | Schoonneveld-Bergmans et al. |
| 2013/0281328 A1 | 10/2013 | Podella et al. |
| 2013/0344554 A1 | 12/2013 | Bleyer et al. |
| 2014/0056853 A1 | 2/2014 | Marrone et al. |
| 2014/0248373 A1 | 9/2014 | Michalow et al. |
| 2015/0045220 A1 | 2/2015 | Michalow et al. |
| 2015/0072917 A1 | 3/2015 | Baldridge et al. |
| 2015/0141311 A1 | 5/2015 | Podella et al. |
| 2015/0191748 A1 | 7/2015 | Dale et al. |
| 2015/0267151 A1 | 9/2015 | Goldfeld et al. |
| 2016/0100587 A1 | 4/2016 | Dywaler-Ekegard et al. |
| 2016/0298056 A1 | 10/2016 | Baldridge et al. |
| 2016/0353746 A1 | 12/2016 | Dale et al. |
| 2016/0362834 A1 | 12/2016 | Dale et al. |
| 2017/0156343 A1 | 6/2017 | Michalow et al. |

FOREIGN PATENT DOCUMENTS

| | | |
|---|---|---|
| EP | 1721966 A1 | 11/2006 |
| WO | 199728092 A1 | 8/1997 |
| WO | 2003037066 A1 | 5/2003 |
| WO | 20050067531 A3 | 7/2005 |
| WO | 2005069849 A2 | 8/2005 |
| WO | 2006119052 A2 | 11/2006 |
| WO | 2010115021 A2 | 7/2010 |
| WO | 2010148535 A1 | 12/2010 |
| WO | 2011016008 A1 | 2/2011 |
| WO | 2013180756 A1 | 12/2013 |
| WO | 2017035099 A1 | 3/2017 |
| WO | 2017035100 A1 | 3/2017 |
| WO | 2017035101 A1 | 3/2017 |

OTHER PUBLICATIONS

Sukumaran et al., "Microbial cellulases—production, applications, and challenges," Journal of Scientific & Industrial Research, vol. 64, Nov. 2005, pp. 832-844.
Frølund, et al., Enzymatic Activity in the Activated-Sludge Floc Matrix, Appl. Microbiol. Biotechnol. 43(3): 755-561 (1995).
EPO, Extended Search Report, EP13796699.0, dated Jul. 12, 2016.
Goel, et al., Enzyme Activities under Anaerobic and Aerobic Conditions in Activated Sludge Sequencing Batch Reactor, Water Research 32(7): 2081-2088 (1998).
PCT Form 237, Written Opinion, PCT/US2013/000140, dated Jul. 22, 2013.
PCT Form IB373, International Preliminary Report on Patentability, PCT/US2013/000140, dated Dec. 2, 2014.
PCT Form 210, International Search Report, PCT/US2016/048092, dated Nov. 15, 2016.
PCT Form 237, Written Opinion, PCT/US2016/048092, dated Nov. 15, 2016.
PCT Form 210, International Search Report, PCT/US2016/048093, dated Oct. 24, 2016.
PCT Form 237, Written Opinion, PCT/US2016/0048093, dated Oct. 24, 2016.
PCT Form 210, International Search Report, PCT/US2016/048094, dated Nov. 4, 2016.
PCT Form 237, Written Opinion, PCT/US2016/048094, dated Nov. 4, 2016.
Sensient Flavors LLC, TASTONE 154, Technical Information (2010).
PCT Form IB373, International Preliminary Report on Patentability, PCT/US2016/048092, pp. 6, dated Feb. 27, 2018.
PCT Form IB373, International Preliminary Report on Patentability, PCT/US2016/048093, pp. 5, dated Feb. 27, 2018.
PCT Form IB373, International Preliminary Report on Patentability, PCT/US2016/048094, pp. 5, dated Feb. 27, 2018.
U.S. Appl. No. 14/404,917, filed May 24, 2013, May 29, 2012, US20150191748, now U.S. Pat. No. 9,617,178.
U.S. Appl. No. 15/444,093, filed Feb. 27, 2017, May 29, 2012, US 20170166467.
U.S. Appl. No. 15/243,958, filed Aug. 22, 2016, May 29, 2012, US20160362834.
U.S. Appl. No. 15/243,961, filed Aug. 22, 2016, May 29, 2012, US20160353746.

* cited by examiner

NON-TOXIC PEST CONTROL COMPOSITIONS AND METHODS AND USES THEREOF

This application is a continuation in part that claims the benefit of priority and the filing date of U.S. patent application Ser. No. 14/404,917, filed on Dec. 1, 2014, a US national stage filing of PCT Patent Application PCT/US2013/000140, filed on May 24, 2013, which claims the benefit of priority and the filing date of U.S. Provisional Patent Application 61/689,077, filed on May 29, 2012; and also claims the benefit of priority and the filing date of U.S. Provisional Patent Application 62/208,662, filed on Aug. 22, 2015, the content of each of which is hereby incorporated by reference in its entirety.

In its broadest sense, a pest refers to any organism that negatively affect a plane and/or animal host organism by colonizing, damaging, attacking, or competing with the host for nutrients or habitat, or directly or indirectly infecting a host organism causing the host's disease or death. Pests can be broadly classified as 1) invertebrate pests, including include insects arachnids, nematodes and gastropods, 2) plant pests and 3) vertebrate pests including mammals and birds. Invertebrate pests.

Pests are detrimental, destructive, and/or troublesome because they adversely affect many human concerns such as public health, the ecology and the economy. For example, infestations of pests 1) spread pathogens or pathogenic vectors causing disease and epidemic outbreaks, 2) decrease agriculture and livestock production by reducing yields and quality, 3) increase structural damage by weakening the physical integrity of buildings, bridges and other man-made structures, and 4) disrupt and ruin native ecosystems by overtaking the habitat of indigenous species. Annually, the worldwide costs associated with pest infestations exceed tens of billions of dollars in terms of the economic loss caused by such infestations as well as the expense associated with keeping pest populations under control.

Pest control is an ongoing, global problem. Historically, pest control has used many means including the use of predators to kill pests, mechanical removal of pest, physical destruction of a pest habitat, and/or baits, traps or other hunting techniques to eliminate pests. However, the predominant and most effective method of pest control is the use of pesticides. A pesticide refers to an agent that can be used to control and/or kill a pest. Pesticides include chemicals discovered through synthetic approaches or natural sources as well as biopesticides, organisms such as, e.g. microbes like bacteria or fungi which are parasitic or otherwise harmful to the pest. Pesticides include algicides, fungicides, herbicides, insecticides (larvicides, adulticides, ovicides), acaricides (miticides), nematicides, molluscicides, rodenticides, parasiticides, as well as other control agents.

However, it is increasingly apparent that the use of current pesticides is falling into disfavor by consumers and regulatory agencies alike due to the detrimental health effects these compound directly cause in humans as well as the damaging environmental effects that are indirectly harmful to ecosystems generally and humans specifically. For instance, there is public and governmental agency concerned about the amount of residual chemicals that persist in food, ground water and the environment, and the risk that these pesticides are toxic, carcinogenic or otherwise incompatible to humans and/or wildlife. Moreover, pests can develop resistance to many commonly used pesticides, calling into question the actual efficacy of these compounds. Based on this increased awareness, current regulatory guidelines encouraged a search for potentially less dangerous pest control products via stringent restrictions on the use of certain pesticides. As a result, elimination of effective pesticides from the market has limited economical and effective options for controlling pests.

Accordingly, there is a great need for pest control compositions that are non-toxic, biodegradable and effective in controlling pest populations and their infestations.

SUMMARY

Aspects of the present specification disclose pest control compositions. The disclosed pest control compositions comprises a treated fermented microbial supernatant and one or more nonionic surfactants. The disclosed pest control compositions may further comprise one or more anionic surfactants. In addition, the disclosed pest control compositions may optionally further comprise an antimicrobial, an abrasive agent, a plant essential oil or any combination thereof. The disclosed pest control compositions are biodegradable and substantially non-toxic to humans, mammals, plants and the environment.

Aspects of the present specification disclose a pest control kit. The disclosed pest control kit comprises a pest control composition disclosed herein and instructions for how to use the compositions to control a population of invertebrate pests.

Aspects of the present specification disclose methods of controlling a population of invertebrate pests. The disclosed methods comprises applying an effective amount of a pest control composition disclosed herein to the population of the invertebrate pests and/or one or more locations where control of the population of the invertebrate pests is desired.

Aspects of the present specification disclose uses of a pest control composition disclosed herein for controlling a population of invertebrate pests. The disclosed uses comprises applying an effective amount of the pest control composition to the population of the invertebrate pests and/or one or more locations where control of the population of the invertebrate pests is desired.

DETAILED DESCRIPTION

The invertebrate cuticle is a multi-layered structure synthesized by the underlying epidermal cell layer that forms an exoskeleton. This multi-functional extracellular structure creates a highly impervious barrier that protects the animal from desiccation and pathogenic infection as well as creates a structural framework that maintains its body morphology and integrity, prevents mechanical damage by environmental insults, and enables locomotion via attachments to body-wall muscles. As such, the invertebrate cuticle plays essential and critical roles in preserving the integrity of the animal and its interactions with the environment.

In nematodes, a mostly syncial epidermal cell layer, termed hypodermis, secretes various proteins from its apical membranes which then are extensively cross-linked by peroxidases on the outer surface of the hypodermis to form a polymerized, proteinacious extracellular matrix. The major component of this flexible extracellular matrix are members of the collagen superfamily. In addition to collagens, a highly cross-linked insoluble class of proteins called cuticlins are associated with the cuticle. Overlying the extracellular matrix is the lipid-rich, trilaminar epicuticle that is itself overlaid by a loosely associated, glycoprotein-rich, negatively charged surface coat (or glycocalyx).

Similarly, in arthropods, a simple cuboidal epithelium secretes the components of the cuticle, but in this case, the component is primarily chitin, a polysaccharide composed of N-acetylglucosamine units, together with proteins, lipids, and catecholamines. Chitin filaments are arranged in the protein matrix where they are cross-linked to the proteins using the catecholamines by the enzymatic activity DOPA decarboxylase and tyrosine hydroxylase. Unlike nematodes, where the collagen-based cuticle is uniformly flexible, the arthropod cuticle is more sophisticated, having regions that are thin and highly flexible and others that are thick and rigid. The degree of rigidity is a function of the type of proteins and the quantity of chitin and catecholamines deposited in that region of the cuticle.

In addition, the organization of an arthropod cuticle is typically more complex, having a procuticle layer that can be subdivided into an endocuticle and exocuticle, and an epicuticle layer that may comprise an inner epicuticle, and outer epicuticle, a wax layer and an outer cement layer. There are also microscopic wax canals in the cuticle. The epicuticle layer and wax canals of the cuticle are the primary protection the insect has to insure the maintenance of its vital body fluids. If an insect loses as little as 10% of these fluids, it will die.

In addition, the cuticle provides protection against most foreign agents such as pesticidal liquids and powders. For this reason, ingestion is the primary method of delivery for conventional pesticides. However, pests will only ingest certain substances and in small amounts. This imposes limits on the types of usable pesticides and their effectiveness. For instance, insects generally will not ingest fatal amounts of dehydrating pesticide.

Without wishing to be limited by its theory, the presently disclosed pest control compositions dissolve, disperse, or otherwise disrupt one or more components of the cuticle present on cuticle bearing invertebrate pests, like nematodes and arthropods, resulting in their death through rapid dehydration or desiccation. This mechanism of action is tied to the ability of the pest control compositions disclosed herein to breech the lipid-based membrane epicuticle layer of the cuticle. Methods of applying the disclosed pest control compositions is effected thorough an external exposure, either by direct application to the pest, indirectly by treating a location where pest control is desired, or any other method that exposes the pest to the disclosed pest control compositions in a manner that provides adequate disruption of one or more components of the cuticle and subsequent dehydration or desiccation of the pest.

Regardless of the theory of operation, the disclosed pest control compositions and methods offer an alternative means of pest control that does not rely on chemicals toxic to humans or the environment. Rather the pest control compositions and methods disclosed herein act by exploiting a natural vulnerability of the pest to its environment, namely dehydration and/or dissection of the pest when the cuticle is breached through the actions of the pest control compositions disclosed herein. In addition, the components of the disclosed pest control compositions been proven to be substantially non-toxic to man and domestic animals and which have minimal adverse effects on wildlife and the environment.

Aspects of the present specification disclose, in part, a pest control composition. A pest control composition disclosed herein comprises a treated fermented microbial supernatant and one or more non-ionic surfactants. The treated fermented microbial supernatant lacks any live microorganisms such as yeast or bacteria, and additionally, lacks any active enzymes, activatable pro-enzymes, or any enzymatic activity. Additionally, the pest control composition itself lacks any live microorganisms such as yeast or bacteria, and additionally, lacks any active enzymes, activatable pro-enzymes, or any enzymatic activity. A pest control composition disclosed herein may be used in the control of agricultural, natural environmental, and domestic/household invertebrate pests and/or cuticle-bearing pests.

In an aspect of this embodiment, a pest control composition disclosed herein comprises, e.g., about 75% to about 99% of treated fermented microbial supernatant and about 1%-25% of one or more non-ionic surfactants. In another aspect of this embodiment, a pest control composition disclosed herein comprises, e.g., about 80% to about 97% of treated fermented microbial supernatant and about 3%-20% of one or more non-ionic surfactants. In yet another aspect of this embodiment, a pest control composition disclosed herein comprises, e.g., about 85% to about 95% of treated fermented microbial supernatant and about 5%-15% of one or more non-ionic surfactants. In still another aspect of this embodiment, a pest control composition disclosed herein comprises, e.g., about 87% to about 93% of treated fermented microbial supernatant and about 7%-13% of one or more non-ionic surfactants. In another aspect of this embodiment, a pest control composition disclosed herein comprises, e.g., about 88% to about 92% of treated fermented microbial supernatant and about 8%-12% of one or more non-ionic surfactants. In another aspect of this embodiment, a pest control composition disclosed herein comprises, e.g., about 89% to about 91% of treated fermented microbial supernatant and about 9%-11% of one or more non-ionic surfactants.

Aspects of the present specification disclose, in part, a fermented microbial supernatant. A fermented microbial supernatant disclosed herein can be prepared by culturing a yeast strain, a bacterial strain, or a combination of both a yeast strain and a bacterial strain in a fermenting medium comprising a sugar source, a malt and a magnesium salt. In an aspect of this embodiment, only a single yeast strain is used in a fermenting medium. In another aspect of this embodiment, two or more different yeast strains are used in a fermenting medium. In yet another aspect of this embodiment, only a single bacterial strain is used in a fermenting medium. In still another aspect of this embodiment, two or more different bacterial strains are used in a fermenting medium. In another aspect of this embodiment, one or more different yeast strains are used in conjunction with one or more different bacteria in a fermenting medium. In yet another aspect of this embodiment, two, three, four, five or more different yeast strains are used in conjunction with two, three, four, five or more different bacteria in a fermenting medium.

A sugar source includes, without limitation, sucrose from molasses, raw cane sugar, soybeans or mixtures thereof. Molasses generally contains up to about 50% sucrose in addition to reducing sugars such as glucose and maltase as well as ash, organic nonsugars and some water. The presence of the sugars of the type found in the molasses is important in encouraging the activity of the enzymes and the yeast bacteria by which they are produced. Although the untreated cane blackstrap molasses is preferred, other molasses such as beet molasses, barrel molasses and the like may also be used as a natural source of the materials required for the enzymatic fermentation. The amount of molasses useful in preparing a fermenting medium disclosed herein is between 40% and about 80% by weight, and preferably between about 55% and about 75% by weight. It will be appreciated that specific amounts of the molasses utilized may be varied to yield optimum compositions desired.

Raw cane sugar is a sugar product which has not been refined and which contains residual molasses as well as other natural impurities. Although it is not clearly understood, it has been found that the presence of raw sugar in the fermentation reaction yields significantly improved properties as compared to the use of refined sugars which contain residual chemicals used in the decolorization and final purification and refinement which may have some deleterious effect on the yeast and malt enzymes. It has been found that optimum biological and enzymatic properties of the disclosed fermenting medium are improved where a portion of the fermentable materials present in the mixture comprises raw sugar. The amount of raw cane sugar useful in preparing a fermenting medium disclosed herein may be about 10% and about 40% by weight, and preferably between about 10% and about 30% by weight. It will be appreciated that specific amounts of the raw cane sugar utilized may be varied to yield optimum compositions desired.

The essential enzymes which advantageously contribute to the fermentation reaction are provided by the malt and the yeast and/or bacteria. The specific malt utilized is preferably a diastatic malt which contains enzymes including diastase, maltase and amylase. The malt also is believed to improve the activity of the yeast and/or bacteria in addition to contributing to the overall potency and activity of the enzymatic composition within the final product mixture. The amount of malt useful in preparing a fermenting medium disclosed herein may be between about 3% and about 15% by weight, and preferably between about 7% and about 12% by weight. It will be appreciated that specific amounts of the malt utilized may be varied to yield optimum compositions desired.

Fermentation is a metabolic process that results in the breakdown of carbohydrates and other complex organic substances into simpler substances like sugars, acids, gases or alcohol. Fermentation can occurs in yeast, bacteria and mold. Fermentation includes ethanol fermentation and lactic acid fermentation. Lactic acid fermentation includes homolactic fermentation and heterolactic fermentation.

A yeast refers to any fermentation fungi that can be produce the needed enzymes for a fermentation reaction that results in, for example the conversion of carbohydrates into carbon dioxide and alcohols. A number of enzymes are produced by the active yeast during the fermentation reaction and include both hydrolytic and oxidative enzymes such as invertase, catalase, lactase, maltase, carboxylase and others. Yeast include yeast strains useful in food processing fermentation, such as, e.g., bean-based fermentation, dough-based fermentation, grain-based fermentation, vegetable-based fermentation, fruit-based fermentation, honey-based fermentation, dairy-based fermentation, fish-based fermentation, meat-based fermentation and tea-based fermentation. A non-exhaustive list of particular yeast genera useful in a fermentation reaction disclosed herein include, but is not limited, *Brettanomyces, Candida, Cyberlindnera, Cystofilobasidium, Debaryomyces, Dekkera, Fusarium, Geotrichum, Issatchenkia, Kazachstania, Kloeckera, Kluyveromyces, Lecanicillium, Mucor, Neurospora, Pediococcus, Penicillium, Pichia, Rhizopus, Rhodosporidium, Rhodotorula, Saccharomyces, Schizosaccharomyces, Thrichosporon, Torulaspora, Torulopsis, Verticillium, Yarrowia, Zygosaccharomyces* and *Zygotorulaspora*. Species of yeast useful in a fermentation reaction disclosed herein belong to, without limitation A non-exhaustive list of particular yeast species useful in a fermentation reaction disclosed herein includes, but is not limited, *B. anomalus, B. bruxellensis, B. claussenii, B. custersianus, B. naardenensis, B. nanus, C. colliculosa, C. exiguous, C. humicola, C. kefyr, C. krusei, C. milleri, C. mycoderma, C. pelliculosa, C. rugose, C. stellate, C. tropicalis, C. utilis, C. valida, C. vini, C. zeylanoides, Cb. mrakii, Cs, infirmominiatum, D. hansenii, D. kloeckeri, Dk. anomala, Dk. bruxellensis, F. domesticum, G. candidum, I. orientalis, K. exigua, K. unispora, Kl. africana, Kl. apis, Kl. javanica, Ku. lactis, Ku. marxianus, Ku. marxianus, L. lecanii, M. hiemalis, M. plumbeus, M. racemosus, M. racemosus, N. intermedia, P. cerevisiae, Pn. album, Pn. camemberti, Pn. caseifulvum, Pn. chrysogenum, Pn. commune, Pn. nalgiovense, Pn. roqueforti, Pn. solitum, Pi. fermentans, R. microspores, Rs. infirmominiatum, Rt. glutinis, Rt. minuta, Rt. rubra, S. bayanus, S. boulardii, S. carlsbergensis, S. cerevisiae, S. eubayanus, S. paradoxus, S. pastorianus, S. rouzii, S. uvarum, Sc. pombe, Th. beigelii, T. delbrueckii, T. franciscae, T. pretoriensis, T. microellipsoides, T. globosa, T. indica, T. maleeae, T. quercuum, To. versatilis, V. lecanii, Y. lipolytica, Z. bailii, Z. bisporus, Z. cidri, Z. fermentati, Z. florentinus, Z. kombuchaensis, Z. lentus, Z. mellis, Z. microellipsoides, Z. mrakii, Z. pseudorouxii* and *Z. rouxii* and *Zt. florentina*. A preferred yeast is *Saccharomyces cerevisiae* commonly available as baker's yeast.

Bacteria refer to any fermentation bacteria that can be produce the needed enzymes for a fermentation reaction that results in, for example the production of alcohols like ethanol or acids like acetic acid, lactic acid and/or succinic acid. A non-exhaustive list of particular bacterial genera useful in a fermentation reaction disclosed herein include, but is not limited, *Acetobacter, Arthrobacter, Aerococcus, Bacillus, Bifidobacterium, Brachybacterium, Brevibacterium, Barnobacterium, Carnobacterium, Corynebacterium, Enterococcus, Escherichia, Gluconacetobacter, Gluconobacter, Hafnia, Halomonas, Kocuria, Lactobacillus, Lactococcus, Leuconostoc, Macrococcus, Microbacterium, Micrococcus, Neisseria, Oenococcus, Pediococcus, Propionibacterium, Proteus, Pseudomonas, Psychrobacter, Salmonella, Sporolactobacillus, Staphylococcus, Streptococcus, Streptomyces, Tetragenococcus, Vagococcus, Weissells* and *Zymomonas*. A non-exhaustive list of particular bacterial species useful in a fermentation reaction disclosed herein includes, but is not limited, *A. aceti, A. fabarum, A. lovaniensis, A. malorum, A. orientalis, A. pasteurianus, A. pasteurianus, A. pomorum, A. syzygii, A. tropicalis, Ar. arilaitensis, Ar. Bergerei, Ar. Globiformis, Ar. nicotianae, Ar. variabilis, B. cereus, B. coagulans, B. licheniformis, B. pumilus, B. sphaericus, B. stearothermophilus, B. subtilis, B. adolescentis, B. animalis, B. bifidum, B. breve, B. infantis, B. lactis, B. longum, B. pseudolongum, B. thermophilum, Br. alimentarium, Br. alimentarium, Br. tyrofermentans, Br. tyrofermentans, Bv. aurantiacum, Bv. casei, Bv. linens, C. divergens, C. maltaromaticum, C. piscicola, C. ammoniagenes, Co. casei, Co. fiavescens, Co. mooreparkense, Co. variabile, E. faecalis, E. faecium, G. azotocaptans, G. diazotrophicus, G. entanii, G. europaeus, G. hansenii, G. johannae, G. oboediens, G. xylinus, Gl. oxydans, H. alvei, Hl. elongate, K. rhizophila, K. rhizophila, K. varians, K. varians, L. acetotolerans, L. acidifarinae, L. acidipiscis, L. alimentarius, L. brevis, L. bucheri, L. cacaonum, L. casei, L. cellobiosus, L. collinoides, L. composti, L. coryniformis, L. crispatus, L. curvatus, L. delbrueckii, L. dextrinicus, L. diolivorans, L. fabifermentans, L. farciminis, L. fermentum, L. gasseri, L. ghanensis, L. hammesii, L. harbinensis, L. helveticus, L. hilgardii, L. homohiochii, L. jensenii, L. john-*

*sonii, L. kefiranofaciens, L. kefiri, L. kimchi, L. kisonensis, L. kunkeei, L. mali, L. manihotivorans, L. mindensis, L. mucosae, L. nagelii, L. namuresis, L. nantesis, L. nodensis, L. oeni, L. otakiensis, L. panis, L. parabrevis, L. parabuchneri, L. paracasei, L. parakefiri, L. paralimentarius, L. paraplantarum, L. pentosus, L. perolens, L. plantarum, L. pobuzihii, L. pontis, L. rapi, L. reuteri, L. rhamnosus, L. rossiae, L. sakei, L. salivarius, L. sanfranciscensis, L. satsumensis, L. secaliphilus, L. senmaizukei, L. siliginis, L. similis, L. spicheri, L. suebicus, L. sunkii, L. tucceti, L. vaccinostercus, L. versmoldesis, L. yamanashiensis, Lc. lactis, Lc. raffinolactis, Le. carnosum, Le. citreum, Le. fallax, Le. holzapfelii, Le. inhae, Le. kimchi, Le. lactis, Le. mesenteroides, Le. palmae, Le. Pseudomesenteroides, M. caseolyticus, Mb. foliorum, Mb gubbeenense, Mc. luteus, Mc. lylae, P. acidilactici, P. pentosaceus, P. acidipropionici, P. freudenreichii, P. jensenii, P. thoenii, Pr. vulgaris, Ps. fluorescens, Py. celer, S. carnosus, S. condiment, S. equorum, S. fleurettii, S. piscifermentans, S. saphrophyticus, S. sciuri, S. simulans, S. succinus, S. vitulinus, S. warneri, S. xylosus, St. cremoris, St. gallollyticus, St. salivarius, St. thermophiles, St. griseus, T. halophilus, T. koreensis, W. beninensis, W. cibaria, W. fabaria, W. ghanesis, W. koreensis, W. paramesenteroides, W. thailandensis,* and *Z. mobilis.*

Mold refer to any fermentation mold that can be produce the needed enzymes for a fermentation reaction that results in, for example the production of alcohols like ethanol or acids like acetic acid, lactic acid and/or succinic acid. A non-exhaustive list of particular mold genera useful in a fermentation reaction disclosed herein include, but is not limited, *Aspergillus.* A non-exhaustive list of particular mold species useful in a fermentation reaction disclosed herein includes, but is not limited, *A. acidus, A. fumigatus, A. niger, A. oryzae,* and *A. sojae.*

It will be appreciated that actual amounts of the various types of enzymes produced will be dependent on a number of factors including the types of molasses and sugar used in preparing the fermentation mixture. However, again it is believed that, in utilizing the molasses and raw sugar, optimum enzyme yields and activity are obtained. In an embodiment, the amount of yeast useful in preparing a fermenting medium disclosed herein may be between about 0.2% and about 5% by weight, and preferably between about 1% and about 3% by weight. It will be appreciated that specific amounts of the yeast utilized may be varied to yield optimum compositions desired.

The presence of a small amount of inorganic catalyst such as a magnesium salt enhances the activity of the enzymes not only during the fermentation reaction but thereafter in the product composition in attacking and decomposing the organic waste materials. A preferred magnesium salt is magnesium sulfate. The amount of magnesium salt useful in preparing a fermenting medium disclosed herein may be between about 0.1% and about 5% by weight, and preferably between about 1% and about 3% by weight. It will be appreciated that specific amounts of the magnesium salt utilized may be varied to yield optimum compositions desired.

To prepare a fermented microbial supernatant, the molasses, sucrose and magnesium salt are added to a suitable amount of warm water. Although the specific amount of water used is not particularly critical, typically suitable amounts of water are from about 2 to about 20 times the total weight of the other ingredients of the fermenting medium used in the fermentation reaction. This amount of water is sufficient to facilitate easy admixture as well as to activate the yeast, bacterial and/or mold and dissolve the other materials. In addition, the temperature of the water cannot be too hot such that the heat inactivates the malt and yeast enzymes needed for fermentation. Thus, for example, water temperatures greater than about 65° C. must be avoided and preferred temperatures are between about 25° C. to about 45° C. The use of cold water may result in unduly slow fermentation reaction rates and, thus, should also be avoided where increased reaction rates are desired. After the molasses, sugar and magnesium salt are effectively mixed and dissolved, the malt and the yeast are added, the mixture stirred and allowed to set until fermentation is essentially complete. The reaction time may be between about 2 and about 5 days at temperatures between about 20° C. and about 45° C. Completion may be readily ascertained by noting that the effervescence of the reacting mixture has substantially subsided. At the end of the fermentation reaction, the fermented microbial culture is centrifuged to remove the "sludge" formed during the fermentation. The resulting fermentation supernatant (typically about 90% to about 98% by weight) is collected for subsequent treatment.

A fermented microbial supernatant contains bio-nutrients, minerals and amino acids. Bio-nutrients are typically present in an amount of from about 0.01% to about 1% of the total weight of fermented microbial supernatant. Each individual bio-nutrient is typically present in an amount of from about 0.00001% to about 0.01% of the total weight of fermented microbial supernatant. Examples of bio-nutrients include, without limitation, biotin, folic acid, glucans like α-glucan and β-glucan, niacin, insotil, pantothenic acid, pyridoxine, riboflavin and thiamine. In aspects of this embodiment, a fermented microbial supernatant disclosed herein comprises, e.g., about 0.00001% to about 0.0011% of biotin, about 0.0006% to about 0.016% of folic acid, about 0.005% to about 15% of niacin, about 0.01% to about 1% of insotil, about 0.00017% to about 0.017% of pantothenic acid, about 0.0006% to about 0.016% of pyrodoxine, about 0.002% to about 0.023% of riboflavin and about 0.001% to about 0.02% of thiamine. In other aspects of this embodiment, a fermented microbial supernatant disclosed herein comprises, e.g., about 0.00006% to about 0.0006% of biotin, about 0.001% to about 0.011% of folic acid, about 0.01% to about 0.1% of niacin, about 0.08% to about 0.18% of insotil, about 0.002% to about 0.012% of pantothenic acid, about 0.001% to about 0.011% of pyrodoxine, about 0.007% to about 0.017% of riboflavin, about 0.003% to about 0.013% of thiamine. In yet other aspects of this embodiment, a fermented microbial supernatant disclosed herein comprises, e.g., about 0.00012% to about 0.0006% of biotin, about 0.001% to about 0.011% of folic acid, about 0.01% to about 0.1% of niacin, about 0.08% to about 0.18% of insotil, about 0.003% to about 0.013% of pantothenic acid, about 0.001% to about 0.011% of pyrodoxine, about 0.008% to about 0.017% of riboflavin, about 0.003% to about 0.013% of thiamine. In still other aspects of this embodiment, a fermented microbial supernatant disclosed herein comprises, e.g., about 0.00009% to about 0.0003% of biotin, about 0.004% to about 0.008% of folic acid, about 0.03% to about 0.07% of niacin, about 0.11% to about 0.15% of insotil, about 0.006% to about 0.01% of pantothenic acid, about 0.004% to about 0.008% of pyrodoxine, about 0.01% to about 0.014% of riboflavin, about 0.006% to about 0.010% of thiamine.

Minerals are typically present in an amount of from about 0.1% to about 20% of the total weight of fermented microbial supernatant. Each individual mineral is typically present in an amount of from about 0.0001% to about 5% of the total weight of fermented microbial supernatant. Examples of minerals include, without limitation, calcium, chromium, copper, iron, magnesium, phosphate, potassium, sodium and zinc. In aspects of this embodiment, a fermented microbial supernatant disclosed herein comprises, e.g., about 0.02% to about 0.3% of calcium, about 0.000002% to about 0.0016% of chromium, about 0.000009% to about 0.0014% of copper, about 0.00005% to about 0.02% of iron, about 0.001% to about 1.3% of magnesium, about 0.2% to about 14% of phosphate, about 0.4% to about 16% of potassium, about 0.2% to about 15% of sodium and about 0.08% to about 13% of zinc. In other aspects of this embodiment, a fermented microbial supernatant disclosed herein comprises, e.g., about 0.07% to about 0.21% of calcium, about 0.000007% to about 0.0011% of chromium, about 0.00004% to about 0.0009% of copper, about 0.0001% to about 0.015% of iron, about 0.005% to about 0.9% of magnesium, about 0.7% to about 9% of phosphate, about 0.9% to about 11% of potassium, about 0.7% to about 10% of sodium and about 0.3% to about 8% of zinc. In yet other aspects of this embodiment, a fermented microbial supernatant disclosed herein comprises, e.g., about 0.05% to about 1% of calcium, about 0.0001% to about 0.0009% of chromium, about 0.00006% to about 0.0007% of copper, about 0.0001% to about 0.013% of iron, about 0.005% to about 1% of magnesium, about 0.1% to about 7% of phosphate, about 0.5% to about 9% of potassium, about 0.5% to about 8% of sodium and about 0.5% to about 6% of zinc. In still other aspects of this embodiment, a fermented microbial supernatant disclosed herein comprises, e.g., about 0.12% to about 0.16% of calcium, about 0.0002% to about 0.0006% of chromium, about 0.00009% to about 0.0004% of copper, about 0.0006% to about 0.01% of iron, about 0.01% to about 0.4% of magnesium, about 1% to about 4% of phosphate, about 2% to about 6% of potassium, about 1% to about 5% of sodium and about 0.8% to about 3% of zinc.

Amino acids are typically present in an amount of from about 20% to about 60% of the total weight of fermented microbial supernatant. Each individual amino acid is typically present in an amount of from about 0.1% to about 15% of the total weight of fermented microbial supernatant. Examples of minerals include, without limitation, alanine, arginine, aspartic acid, cysteine, glutamic acid, glycine, lysine, methionine, phenylalanine, proline, serine, and threonine. In aspects of this embodiment, a fermented microbial supernatant disclosed herein comprises, e.g., about 0.2% to about 16% of alanine, about 0.09% to about 15% of arginine, about 0.4% to about 18% of aspartic acid, about 0.003% to about 5% of cysteine, about 0.5% to about 20% of glutamic acid, about 0.09% to about 15% of glycine, about 0.09% to about 15% of lysine, about 0.002% to about 5% of methionine, about 0.09% to about 15% of phenylalanine, about 0.09% to about 15% of proline, about 0.09% to about 15% of serine and about 0.09% to about 15% of threonine. In other aspects of this embodiment, a fermented microbial supernatant disclosed herein comprises, e.g., about 0.7% to about 11% of alanine, about 0.5% to about 10% of arginine, about 0.9% to about 13% of aspartic acid, about 0.008% to about 1.2% of cysteine, about 1% to about 15% of glutamic acid, about 0.5% to about 10% of glycine, about 0.8% to about 12% of lysine, about 0.2% to about 1.6% of methionine, about 0.5% to about 10% of phenylalanine, about 0.5% to about 10% of proline, about 0.5% to about 10% of serine and about 0.5% to about 10% of threonine. In yet other aspects of this embodiment, a fermented microbial supernatant disclosed herein comprises, e.g., about 0.5% to about 9% of alanine, about 0.5% to about 8% of arginine, about 1% to about 11% of aspartic acid, about 0.01% to about 2% of cysteine, about 3% to about 13% of glutamic acid, about 0.5% to about 8% of glycine, about 1% to about 10% of lysine, about 0.3% to about 3% of methionine, about 0.5% to about 7% of phenylalanine, about 0.5% to about 7% of proline, about 0.5% to about 7% of serine and about 0.5% to about 7% of threonine. In sill other aspects of this embodiment, a fermented microbial supernatant disclosed herein comprises, e.g., about 2% to about 6% of alanine, about 1% to about 5% of arginine, about 4% to about 8% of aspartic acid, about 0.03% to about 0.7% of cysteine, about 6% to about 10% of glutamic acid, about 1% to about 5% of glycine, about 3% to about 7% of lysine, about 0.7% to about 1.1% of methionine, about 1% to about 5% of phenylalanine, about 1% to about 5% of proline, about 1% to about 5% of serine and about 1% to about 5% of threonine.

Aspects of the present specification disclose, in part, a treated fermented microbial supernatant. A treated fermented microbial supernatant is one that is processed in a manner that denatures, kills or otherwise destroys any remaining live yeast, active enzymes contributed by the yeast and malt as well as any other microorganism or enzymes contributed by another source present in a fermented microbial supernatant disclosed herein. Non-limiting examples, of useful treatment procedures include a boiling process using high temperatures, an autoclaving process using high temperatures and high pressure or an irradiation process by exposing the supernatant to ionizing radiation, or any other sterilization process that denatures, kills or otherwise destroys any remaining live yeast, active enzymes contributed by the yeast and malt as well as any other microorganism or enzymes contributed by another source present in a fermented microbial supernatant disclosed herein. Furthermore, the above treatment processes could be used alone, in combination with one another, or in combination with a pasteurization process, a chemical sterilization process and a sterile filtration process to denature, kill or otherwise destroys proteins such as enzymes and microorganisms such as yeast, bacteria and/or mold present the fermentation supernatant disclosed herein. All the methods discussed above are processes known to a person of ordinary skilled in the art as these are routinely used in the food preparation and/or sterilization arts.

The treated fermented microbial supernatant can then be stored in liquid form for subsequent use. Alternatively, the treated fermented microbial supernatant can be spray dried by methods known in the art to produce a dry powder. The dry powder form can also be stored for subsequent use.

Any amount of treated fermented microbial supernatant disclosed herein may be used in a disclosed pest control composition, with the proviso that the amount is useful to practice the methods disclosed herein. Factor used in determining an appropriate amount include, e.g., whether the treated fermented microbial supernatant is in liquid or powder form, the particular commercial source of the treated fermented microbial supernatant, the particular method used to produce the treated fermented microbial supernatant, whether the pest control composition is produced as a concentrate or as a ready as is product, and the dilution factor desired when preparing pest control composition from a concentrate. Typically, a larger amount of a liquid form of the treated fermented microbial supernatant will be required relative to a dry powder form.

In aspects of this embodiment, the amount of treated fermented microbial supernatant used is, e.g., about 0.5% by weight, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 6.0% by weight, about 7.0% by weight, about 7.5% by weight, about 8.0% by weight, about 9.0% by weight or about 10.0% by weight. In other aspects of this embodiment, the amount of treated fermented microbial supernatant used is, e.g., at least 0.5% by weight, at least 1.0% by weight, at least 1.5% by weight, at least 2.0% by weight, at least 2.5% by weight, at least 3.0% by weight, at least 3.5% by weight, at least 4.0% by weight, at least 4.5% by weight, at least 5.0% by weight, at least 6.0% by weight, at least 7.0% by weight, at least 7.5% by weight, at least 8.0% by weight, at least 9.0% by weight or at least 10.0% by weight. In yet other aspects of this embodiment, the amount of treated fermented microbial supernatant used is, e.g., at most 0.5% by weight, at most 1.0% by weight, at most 1.5% by weight, at most 2.0% by weight, at most 2.5% by weight, at most 3.0% by weight, at most 3.5% by weight, at most 4.0% by weight, at most 4.5% by weight, at most 5.0% by weight, at most 6.0% by weight, at most 7.0% by weight, at most 7.5% by weight, at most 8.0% by weight, at most 9.0% by weight or at most 10.0% by weight. In still other aspects of this embodiment, the amount of treated fermented microbial supernatant used is between, e.g., about 0.1% to about 2.5% by weight, about 0.1% to about 3.0% by weight, about 0.1% to about 3.5% by weight, about 0.1% to about 4.0% by weight, about 0.1% to about 5.0% by weight, about 0.5% to about 2.5% by weight, about 0.5% to about 3.0% by weight, about 0.5% to about 3.5% by weight, about 0.5% to about 4.0% by weight, about 0.5% to about 5.0% by weight, about 1% to about 2.5% by weight, about 1% to about 3.0% by weight, about 1% to about 3.5% by weight, about 1% to about 4.0% by weight, about 1% to about 5.0% by weight, about 1% to about 6.0% by weight, about 1% to about 7.0% by weight, about 1% to about 8.0% by weight, about 1% to about 9.0% by weight or about 1% to about 10.0% by weight.

In other aspects of this embodiment, the amount of treated fermented microbial supernatant used is, e.g., about 15.0% by weight, about 20.0% by weight, about 25.0% by weight, about 30.0% by weight, about 35.0% by weight, about 40.0% by weight, about 45.0% by weight, about 50.0% by weight, about 55.0% by weight, about 60.0% by weight, about 65.0% by weight, about 70.0% by weight, about 75.0% by weight, about 80.0% by weight, about 85.0% by weight or about 90.0% by weight. In yet other aspects of this embodiment, the amount of treated fermented microbial supernatant used is, e.g., at least 15.0% by weight, at least 20.0% by weight, at least 25.0% by weight, at least 30.0% by weight, at least 35.0% by weight, at least 40.0% by weight, at least 45.0% by weight, at least 50.0% by weight, at least 55.0% by weight, at least 60.0% by weight, at least 65.0% by weight, at least 70.0% by weight, at least 75.0% by weight, at least 80.0% by weight, at least 85.0% by weight or at least 90.0% by weight. In still other aspects of this embodiment, the amount of treated fermented microbial supernatant used is, e.g., at most 15.0% by weight, at most 20.0% by weight, at most 25.0% by weight, at most 30.0% by weight, at most 35.0% by weight, at most 40.0% by weight, at most 45.0% by weight, at most 50.0% by weight, at most 55.0% by weight, at most 60.0% by weight, at most 65.0% by weight, at most 70.0% by weight, at most 75.0% by weight, at most 80.0% by weight, at most 85.0% by weight or at most 90.0% by weight.

In other aspects of this embodiment, the amount of treated fermented microbial supernatant used is between, e.g., about 5% to about 7.5% by weight, about 5% to about 10% by weight, about 5% to about 15% by weight, about 5% to about 20% by weight, about 5% to about 25% by weight, about 5% to about 30% by weight, about 5% to about 35% by weight, about 5% to about 40% by weight, about 5% to about 45% by weight, about 5% to about 50% by weight, about 5% to about 55% by weight, about 5% to about 60% by weight, about 5% to about 65% by weight, about 5% to about 70% by weight, about 5% to about 75% by weight, about 5% to about 80% by weight, about 5% to about 85% by weight, about 5% to about 90% by weight, about 5% to about 95% by weight, about 10% to about 15% by weight, about 10% to about 20% by weight, about 10% to about 25% by weight, about 10% to about 30% by weight, about 10% to about 35% by weight, about 10% to about 40% by weight, about 10% to about 45% by weight, about 10% to about 50% by weight, about 10% to about 55% by weight, about 10% to about 60% by weight, about 10% to about 65% by weight, about 10% to about 70% by weight, about 10% to about 75% by weight, about 10% to about 80% by weight, about 10% to about 85% by weight, about 10% to about 90% by weight, about 10% to about 95% by weight, about 15% to about 20% by weight, about 15% to about 25% by weight, about 15% to about 30% by weight, about 15% to about 35% by weight, about 15% to about 40% by weight, about 15% to about 45% by weight, about 15% to about 50% by weight, about 15% to about 55% by weight, about 15% to about 60% by weight, about 15% to about 65% by weight, about 15% to about 70% by weight, about 15% to about 75% by weight, about 15% to about 80% by weight, about 15% to about 85% by weight, about 15% to about 90% by weight, about 15% to about 95% by weight, about 25% to about 25% by weight, about 25% to about 30% by weight, about 25% to about 35% by weight, about 25% to about 40% by weight, about 25% to about 45% by weight, about 25% to about 50% by weight, about 25% to about 55% by weight, about 25% to about 60% by weight, about 25% to about 65% by weight, about 25% to about 70% by weight, about 25% to about 75% by weight, about 25% to about 80% by weight, about 25% to about 85% by weight, about 25% to about 90% by weight, about 25% to about 95% by weight, about 25% to about 30% by weight, about 25% to about 35% by weight, about 25% to about 40% by weight, about 25% to about 45% by weight, about 25% to about 50% by weight, about 25% to about 55% by weight, about 25% to about 60% by weight, about 25% to about 65% by weight, about 25% to about 70% by weight, about 25% to about 75% by weight, about 25% to about 80% by weight, about 25% to about 85% by weight, about 25% to about 90% by weight, about 25% to about 95% by weight, about 30% to about 35% by weight, about 30% to about 40% by weight, about 30% to about 45% by weight, about 30% to about 50% by weight, about 30% to about 55% by weight, about 30% to about 60% by weight, about 30% to about 65% by weight, about 30% to about 70% by weight, about 30% to about 75% by weight, about 30% to about 80% by weight, about 30% to about 85% by weight, about 30% to about 90% by weight, about 30% to about 95% by weight, about 35% to about 40% by weight, about 35% to about 45% by weight, about 35% to about 50% by weight, about 35% to about 55% by weight, about 35% to about 60% by weight, about 35% to about 65% by weight, about 35% to about 70% by weight, about 35% to about 75% by weight, about 35% to about 80% by weight, about 35% to about 85% by weight, about 35% to about 90% by weight, about 35% to about 95% by weight, about 40% to about 45% by weight, about 40% to about 50% by weight, about 40% to about 55% by weight, about 40% to about 60% by weight, about 40% to about 65% by weight, about 40% to about 70% by weight, about 40% to about 75% by weight, about 40% to about 80% by weight, about 40% to about 85% by weight, about 40% to about 90% by weight, about 40% to about 95% by weight, about 45% to about 50% by weight, about 45% to about 55% by weight, about 45% to about 60% by weight, about 45% to about 65% by weight, about 45% to about 70% by weight, about 45% to about 75% by weight, about 45% to about 80% by weight, about 45% to about 85% by weight, about 45% to about 90% by weight, about 45% to about 95% by weight, about 50% to about 55% by weight, about 50% to about 60% by weight, about 50% to about 65% by weight, about 50% to about 70% by weight, about 50% to about 75% by weight, about 50% to about 80% by weight, about 50% to about 85% by weight, about 50% to about 90% by weight, about 50% to about 95% by weight, about 55% to about 60% by weight, about 55% to about 65% by weight, about 55% to about 70% by weight, about 55% to about 75% by weight, about 55% to about 80% by weight, about 55% to about 85% by weight, about 55% to about 90% by weight, about 55% to about 95% by weight, about 60% to about 65% by weight, about 60% to about 70% by weight, about 60% to about 75% by weight, about 60% to about 80% by weight, about 60% to about 85% by weight, about 60% to about 90% by weight, about 60% to about 95% by weight, about 65% to about 70% by weight, about 65% to about 75% by weight, about 65% to about 80% by weight, about 65% to about 85% by weight, about 65% to about 90% by weight, about 65% to about 95% by weight, about 70% to about 75% by weight, about 70% to about 80% by weight, about 70% to about 85% by weight, about 70% to about 90% by weight, about 70% to about 95% by weight, about 75% to about 80% by weight, about 75% to about 85% by weight, about 75% to about 90% by weight, about 75% to about 95% by weight, about 80% to about 85% by weight, about 80% to about 90% by weight, about 80% to about 95% by weight, about 85% to about 90% by weight, about 85% to about 95% by weight or about 90% to about 95% by weight.

Aspects of the present specification disclose, in part, a surfactant. Surfactants are compounds that lower the surface tension of a liquid, allowing easier spreading, and lowering of the interfacial tension between two liquids, or between a liquid and a solid. Either a single surfactant may be mixed with the buffered solution disclosed herein, or a plurality of surfactants may be mixed with the buffered solution disclosed herein. Useful surfactants, include, without limitation, ionic surfactants, zwitterionic (amphoteric) surfactants, non-ionic surfactants, or any combination therein. The surfactant used in a method disclosed herein can be varied as appropriate by one skilled in the art and generally depends, in part, on the particular buffer being used, the protein being eluted, and the conductivity values being employed.

Ionic surfactants include anionic surfactants. Anionic surfactants include ones based on permanent functional groups attached to the head, such as, e.g., sulfate, sulfonate, phosphate carboxylates) or pH dependent anionic surfactants. Anionic surfactants include, without limitation, alkyl sulfates like ammonium lauryl sulfate and sodium lauryl sulfate (SDS); alkyl ether sulfates like sodium laureth sulfate and sodium myreth sulfate; docusates like dioctyl sodium sulfosuccinate; sulfonate fluorosurfactants like perfluorooctanesulfonate (PFOS) and perfluorobutanesulfonate; alkyl-diphenyloxide Disulfonates like DOWFAX™ 2A1 (Disodium Lauryl Phenyl Ether Disulfonate), DOWFAX™ 3B2 (Disodium Decyl Phenyl Ether Disulfonate), DOWFAX™ C10L (Disodium Decyl Phenyl Ether Disulfonate), DOWFAX™ 2EP, and DOWFAX™ 8390 (Disodium Cetyl Phenyl Ether Disulfonate); potassium phosphate polyether esters like TRITON™ H-55 and TRITON™ H-66; alkyl benzene sulfonates; alkyl aryl ether phosphates; alkyl ether phosphates; alkyl carboxylates like fatty acid salts and sodium stearate; sodium lauroyl sarcosinate; carboxylate fluorosurfactants like perfluorononanoate and perfluorooctanoate; and Sodium Hexyldiphenyl Ether Sulfonate (DOWFAX™ C6L).

Ionic surfactants also include cationic surfactants. Cationic surfactants include ones based on permanent or pH dependent cationic surfactants, such as, e.g., primary, secondary or tertiary amines. Cationic surfactants include, without limitation, alkyltrimethylammonium salts like cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; and dioctadecyldimethylammonium bromide (DODAB), as well as pH-dependent primary, secondary or tertiary amines like surfactants where the primary amines become positively charged at pH greater than 10, or the secondary amines become charged at pH less than 4, like octenidine dihydrochloride. Other useful anionic surfactants include bio-based anionic surfactants, including, without limitation, STEPONOL® AM 30-KE, an ammonium lauryl sulfate, and STEPONOL® EHS, a sodium 2-ethyl hexyl sulfate. Such bio-based surfactants are not synthetic molecules, but instead are anionic biosurfactants derived from organic matter such as plants.

Zwitterionic surfactants are based on primary, secondary or tertiary amines or quaternary ammonium cation with a sulfonate, a carboxylate, or a phosphate. Zwitterionic surfactants include, without limitation, 3-[(3-Cholamidopropyl)dimethylammonio]-1-propanesulfonate (CHAPS); sultaines like cocamidopropyl hydroxysultaine; betaines like cocamidopropyl betaine; or lecithins.

Non-ionic surfactants are less denaturing and as such are useful to solubilize membrane proteins and lipids while retaining protein-protein interactions. Nonionic surfactant include polyether nonionic surfactants, polyhydroxyl nonionic surfactants and biosurfactants. Nonionic surfactant include alcohol ethoxylates, alkylphenol ethoxylates, phenol ethoxylates, amide ethoxylates, glyceride ethoxylates, fatty acid ethoxylates, and fatty amine ethoxylates. A nonionic surfactant disclosed herein may have the general formula of $H(OCH_2CH_2)_xOC_5H_4R^1$, $(OCH_2CH_2)_xOR^2$, or $H(OCH_2CH_2)_xOC(O)R^2$, wherein x represents the number of moles of ethylene oxide added to an alkyl phenol and/or a fatty alcohol or a fatty acid, $R^1$ represents a long chain alkyl group and, $R^2$ represents a long chain aliphatic group. In aspects of this embodiment, $R^1$ is a $C_7$-$C_{10}$ alkyl group and/or $R^2$ is a $C_{12}$-$C_{20}$ aliphatic group. Other useful non-ionic surfactants include bio-based non-ionic surfactants, including, without limitation, STEPOSOL® MET-10U, a metathesis-derived, nonionic surfactant that is an unsaturated, short chain amide. Such bio-based surfactants are not synthetic molecules, but instead are non-ionic biosurfactants derived from organic matter such as plants.

Non-limiting examples of surfactants include polyoxyethylene glycol sorbitan alkyl esters (or ethoxylated sorbital esters) like polysorbate 20 sorbitan monooleate (TWEEN® 20), polysorbate 40 sorbitan monooleate (TWEEN® 40), polysorbate 60 sorbitan monooleate (TWEEN® 60), polysorbate 61 sorbitan monooleate (TWEEN® 61), polysorbate 65 sorbitan monooleate (TWEEN® 65), polysorbate 80 sorbitan monooleate (TWEEN® 80), polysorbate 81 sorbitan monooleate (TWEEN® 81) and polysorbate 85 sorbitan monooleate (TWEEN® 85); sorbital esters like sorbitan monooleate, sorbitan monolaurate, sorbitan monopalmitate, sorbitan monostearate and sorbitan tristearate; polyglycerol esters like glycerol monooleate, glycerol monolaurate, glycerol monopalmitate, glycerol monostearate, glycerol trioleate, glycerol ricinoleate, glycerol tristearate, mono diglycerides and glycerol triacetate; ethoxylated polyglycerol esters; alkyl glucosides like arachidyl glucoside, $C_{12-20}$ alkyl glucoside, caprylyl/capryl glucoside, cetearyl glucoside, coco-glucoside, ethyl glucoside and lauryl glucoside. decyl glucoside; ethoxylated alkyl glucosides; sucrose esters like sucrose monooleate, sucrose monolaurate, sucrose monopalmitate, sucrose monostearate, sucrose trioleate, sucrose ricinoleate, sucrose tristearate, sucrose diglycerides and sucrose triacetate; ethoxylated sucrose ester; amine oxides; ethoxylated alcohols; ethoxylated aliphatic alcohols; alkylamines; ethoxylated alkylamines; ethoxylated alkyl phenols like ethoxylated nonyl phenol and ethoxylated octyl phenol; alkyl polysaccharides; ethoxylated alkyl polysaccharides; ethoxylated fatty acids like ethoxylated castor oil; ethoxylated fatty alcohols like ethoxylated ceto-oleyl alcohol, ethoxylated ceto-stearyl alcohol, ethoxylated decyl alcohol, ethoxylated dodecyl alcohol and ethoxylated tridecyl alcohol; ethoxylated fatty amines; poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and Poloxamer 407 (PLURONIC® F127); linear secondary alcohol ethoxylates like TERGITOL™ 15-S-5, TERGITOL™ 15-S-7, TERGITOL™ 15-S-9, TERGITOL™ 15-S-12, TERGITOL™ 15-S-15, TERGITOL™ 15-S-20, TERGITOL™ 15-S-30 and TERGITOL™ 15-S-40; alkyl phenol polyglycol ethers; polyethylene glycol alkyl aryl ethers; polyoxyethylene glycol alkyl ethers, like octaethylene glycol monododecyl ether, pentaethylene glycol monododecyl ether, BRIJ® 30, and BRIJ® 35; 2-dodecoxyethanol (LUBROL®-PX); polyoxyethylene glycol octylphenol ethers like polyoxyethylene (4-5) p-t-octyl phenol (TRITON® X-45) and polyoxyethylene octyl phenyl ether (TRITON® X-100); polyoxyethylene glycol alkylphenol ethers like Nonoxynol-9; phenoxypolyethoxylethanols like nonylphenoxypolyethoxylethanol and octylphenoxypolyethoxylethanol (IGEPAL® CA-630 or NONIDET™ P-40); glucoside alkyl ethers like octyl glucopyranoside; maltoside alkyl ethers like dodecyl maltopyranoside; thioglucoside alkyl ethers like heptyl thioglucopyranoside; digitonins; glycerol alkyl esters like glyceryl laurate; alkyl aryl polyether sulfates; alcohol sulfonates; sorbitan alkyl esters; cocamide ethanolamines like cocamide monoethanolamine and cocamide diethanolamine; sucrose monolaurate; dodecyl dimethylamine oxide, and sodium cholate. Other non-limiting examples of surfactants useful in the methods disclosed herein can be found in, e.g., Winslow, et al., *Methods and Compositions for Simultaneously Isolating Hemoglobin from Red Blood Cells and Inactivating Viruses*, U.S. 2008/0138790; Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

Non-ionic surfactants act synergistically to enhance the action of the fermentated microbial supernatant. In addition, it has been established that the non-ionic surfactants used in the pest control compositions disclosed herein are compatible with enhance chemical reactions. Thus, in an embodiment, a pest control composition disclosed herein contains only one or more nonionic surfactants. In another embodiment, a pest control composition disclosed herein contains only one or more nonionic surfactants and one or more anionic surfactants. In another embodiment, a pest control composition disclosed herein does not contain any cationic surfactants. In another embodiment, a pest control composition disclosed herein does not contain any cationic surfactants or zwitterionic surfactants. In another embodiment, a pest control composition disclosed herein does not contain any ionic surfactants. In another embodiment, a pest control composition disclosed herein does not contain any ionic surfactants or zwitterionic surfactants.

Any amount of surfactant disclosed herein may be used, with the proviso that the amount is useful to practice the methods disclosed herein. In aspects of this embodiment, the amount of surfactant used is, e.g., about 0.01% by weight, about 0.05% by weight, about 0.075% by weight, about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.5% by weight, about 2.0% by weight, about 2.5% by weight, about 3.0% by weight, about 4.0% by weight, about 5.0% by weight, about 6.0% by weight, about 7.0% by weight, about 7.5% by weight, about 8.0% by weight, about 9.0% by weight or about 10.0% by weight. In other aspects of this embodiment, the amount of surfactant used is, e.g., at least 0.01% by weight, at least 0.05% by weight, at least 0.075% by weight, at least 0.1% by weight, at least 0.25% by weight, at least 0.5% by weight, at least 0.75% by weight, at least 1.0% by weight, at least 1.5% by weight, at least 2.0% by weight, at least 2.5% by weight, at least 3.0% by weight, at least 4.0% by weight, at least 5.0% by weight, at least 6.0% by weight, at least 7.0% by weight, at least 7.5% by weight, at least 8.0% by weight, at least 9.0% by weight, or at least 10.0% by weight. In yet other aspects of this embodiment, the amount of surfactant used is, e.g., at most 0.01% by weight, at most 0.05% by weight, at most 0.075% by weight, at most 0.1% by weight, at most 0.25% by weight, at most 0.5% by weight, at most 0.75% by weight, at most 1.0% by weight, at most 1.5% by weight, at most 2.0% by weight, at most 2.5% by weight, at most 3.0% by weight, at most 4.0% by weight, at most 5.0% by weight, at most 6.0% by weight, at most 7.5% by weight, at most 8.0% by weight, at most 9.0% by weight or at most 10.0% by weight.

In still other aspects of this embodiment, the amount of surfactant used is between, e.g., about 0.1% by weight to about 0.5% by weight, about 0.1% by weight to about 0.75% by weight, about 0.1% by weight to about 1.0% by weight, about 0.1% by weight to about 1.5% by weight, about 0.1% by weight to about 2.0% by weight, about 0.1% by weight to about 2.5% by weight, about 0.2% by weight to about 0.5% by weight, about 0.2% by weight to about 0.75% by weight, about 0.2% by weight to about 1.0% by weight, about 0.2% by weight to about 1.5% by weight, about 0.2% by weight to about 2.0% by weight, about 0.2% by weight to about 2.5% by weight, about 0.5% by weight to about 1.0% by weight, about 0.5% by weight to about 1.5% by weight, about 0.5% by weight to about 2.0% by weight, about 0.5% by weight to about 2.5% by weight, about 0.5% by weight to about 3.0% by weight, about 0.5% by weight to about 4.0% by weight, about 0.5% by weight to about 5.0% by weight, about 1.0% by weight to about 2.5% by weight, about 1.0% by weight to about 3.0% by weight, about 1.0% by weight to about 4.0% by weight, about 1.0% by weight to about 5.0% by weight, about 1.0% by weight to about 6.0% by weight, about 1.0% by weight to about 7.0% by weight, about 1.0% by weight to about 7.5% by weight, about 1.0% by weight to about 8.0% by weight, about 1.0% by weight to about 9.0% by weight, about 1.0% by weight to about 10.0% by weight, about 2.0% by weight to about 2.5% by weight, about 2.0% by weight to about 3.0% by weight, about 2.0% by weight to about 4.0% by weight, about 2.0% by weight to about 5.0% by weight, about 2.0% by weight to about 6.0% by weight, about 2.0% by weight to about 7.0% by weight, about 2.0% by weight to about 7.5% by weight, about 2.0% by weight to about 8.0% by weight, about 2.0% by weight to about 9.0% by weight, about 2.0% by weight to about 10.0% by weight, about 5.0% by weight to about 6.0% by weight, about 5.0% by weight to about 7.0% by weight, about 5.0% by weight to about 7.5% by weight, about 5.0% by weight to about 8.0% by weight, about 5.0% by weight to about 9.0% by weight, about 5.0% by weight to about 10.0% by weight, about 5.0% by weight to about 11.0% by weight, about 5.0% by weight to about 12.0% by weight, about 5.0% by weight to about 13.0% by weight, about 5.0% by weight to about 14.0% by weight or about 5.0% by weight to about 15.0% by weight.

Aspects of the present specification disclose, in part, a pH of a pest control composition disclosed herein. The final pH of a pest control composition is typically acidic as this contributes to a longer shelf-life of the composition. In aspects of this embodiment, the pH of a pest control composition disclosed herein is, e.g., about 2, about 2.5, about 3, about 3.5, about 4, about 4.5, about 5, about 5.5 or about 6. In other aspects of this embodiment, the pH of a pest control composition disclosed herein is, e.g., at least 2, at least 2.5, at least 3, at least 3.5, at least 4, at least 4.5, at least 5, at least 5.5 or at least 6. In yet other aspects of this embodiment, the pH of a pest control composition disclosed herein is, e.g., at most 2, at most 2.5, at most 3, at most 3.5, at most 4, at most 4.5, at most 5, at most 5.5 or at most 6. In still other aspects of this embodiment, the pH of a pest control composition disclosed herein is between, e.g., about 2 to about 3, about 2 to about 3.5, about 2 to about 4, about 2 to about 4.5, about 2 to about 5, about 2 to about 5.5, about 2 to about 6, about 2.5 to about 3, about 2.5 to about 3.5, about 2.5 to about 4, about 2.5 to about 4.5, about 2.5 to about 5, about 2.5 to about 5.5, about 2.5 to about 6, about 3 to about 3.5, about 3 to about 4, about 3 to about 4.2, about 3 to about 4.5, about 3 to about 4.7, about 3 to about 5, about 3 to about 5.2, about 3 to about 5.5, about 3 to about 6, about 3.5 to about 4, about 3.5 to about 4.2, about 3.5 to about 4.5, about 3.5 to about 4.7, about 3.5 to about 5, about 3.5 to about 5.2, about 3.5 to about 5.5, about 3.5 to about 6, about 3.7 to about 4.0, about 3.7 to about 4.2, about 3.7 to about 4.5, about 3.7 to about 5.2, about 3.7 to about 5.5 or about 3.7 to about 6.0.

Aspects of the present specification disclose, in part, an antimicrobial. A pest control composition disclosed herein may optionally further comprise an antimicrobial. Alternatively, a pest control composition disclosed herein may not comprise an antimicrobial. A method or use disclosed herein may further comprising applying an additional composition comprising an antimicrobial. Alternatively, method or use disclosed herein may not further include a step of applying an additional composition comprising an antimicrobial. Antimicrobials are compounds that can kill a microorganisms, exert a growth inhibit effect or otherwise deter, render harmless, or exert a controlling effect on a microorganism. Non-limiting examples of an antimicrobial include an antibacterial, an antifungal, an antiviral and antiparasitic.

Aspects of the present specification disclose, in part, an abrasive agent. A pest control composition disclosed herein may optionally further comprise an abrasive agent. Alternatively, a pest control composition disclosed herein may not comprise an abrasive agent. An abrasive agent disclosed herein is a material that mechanically abrades and/or punctures the cuticle of an invertebrate pest breeching it in a manner that provides adequate disruption to cause subsequent dehydration or desiccation of the pest. Although an abrasive agent is typically slow acting, causing a gradual reduction in activity, slow loss of weight, and eventual death, when used as a component of a pest control compositions disclosed herein, the combined effects of all components is accelerated and/or enhanced. An abrasive agent includes, without limitation, diatomaceous earth, sodium bicarbonate, calcium carbonate and amorphous silica. An abrasive agent disclosed herein can also have absorbent or dehydrating properties which provides further dehydration or desiccation of a pest so exposed.

Aspects of the present specification disclose, in part, a plant essential oil. A pest control composition disclosed herein may optionally further comprise a plant essential oil. Alternatively, a pest control composition disclosed herein may not comprise a plant essential oil. An essential oil may act as a solvent against the cuticle of an invertebrate pest, thereby penetrating the cuticle and causing mortality. A plant essential oil may penetrate the cuticle and contact the nerve endings in the invertebrate pest's trachea, and cause neurotoxic activity. As such, use of a plant essential oil enhances and/or accelerates the pest controlling activities of a pest control composition disclosed herein. Plant essential oils useful in a pest control composition disclosed herein are described in, e.g., U.S. Pat. Nos. 8,877,219, 7,988,985, 7,618,645 and 7,109,240, each of which is incorporated by reference in its entirety.

A plant essential oil or derivative thereof may be extracted from a natural source or synthetically made and include racemic mixtures, enantiomers, diastereomers, hydrates, salts, solvates and metabolites, etc. Such oils generally contains as a major constituent an acyclic monoterpene alcohol or aldehyde, a benzenoid aromatic compound containing at least one oxygenated substituent or side chain, or a monocarbocyclic terpene generally having a six membered ring bearing one or more oxygenated substituents. Examples of suitable plant essential oils disclosed herein include, without limitation, α- or β-pinene; α-campholenic aldehyde; α-citronellol; α-iso-amyl-cinnamic (e.g., amyl cinnamic aldehyde); α-pinene oxide; α-cinnamic terpinene; α-terpineol (e.g., 1-methyl-4-isopropyl-1-cyclohexen-8-ol); λ-terpinene; achillea; aldehyde C16 (pure); α-phellandrene; amyl cinnamic aldehyde; amyl salicylate; anethole; anise; aniseed; anisic aldehyde; basil; bay; benzyl acetate; benzyl alcohol; bergamot (e.g., *Monardia fistulosa, Monarda didyma, Citrus bergamia, Monarda punctata*); bitter orange peel; black pepper; borneol; calamus; camphor; cananga oil (e.g., java); cardamom; carnation (e.g., *dianthus caryophyllus*); carvacrol; carveol; cassia; castor; cedar (e.g., hinoki); cedarwood; chamomile; cineole; cinnamaldehyde; cinnamic alcohol; cinnamon; cis-pinane; citral (e.g., 3,7-dimethyl-2, 6-octadienal); citronella; citronellal; citronellol dextro (e.g., 3-7-dimethyl-6-octen-1-ol); citronellol; citronellyl acetate; citronellyl nitrile; *citrus unshiu*; clary sage; clove (e.g., *eugenia caryophyllus*); clove bud; coriander; corn; cotton seed; d-dihydrocarvone; decyl aldehyde; diethyl phthalate;

dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin (e.g., 3-ethoxy-4-hydrobenzaldehyde); eucalyptol (e.g., cineole); eucalyptus citriodora; eucalyptus globulus; eucalyptus; eugenol (e.g., 2-methoxy-4-allyl phenol); evening primrose; fenchol; fennel; Ferniol™; fish; florazon (e.g., 4-ethyl-α, α-dimethyl-benzenepropanal); galaxolide; geraniol (e.g., 2-trans-3,7-dimethyl-2,6-octadien-8-ol); geraniol; geranium; geranyl acetate; geranyl nitrile; ginger; grapefruit; guaiacol; guaiacwood; gurjun balsam; heliotropin; herbanate (e.g., 3-(1-methyl-ethyl) bicyclo(2,2,1) hept-5-ene-2-carboxylic acid ethyl ester); hiba; hydroxycitronellal; i-carvone; i-methyl acetate; ionone; isobutyl quinoleine (e.g., 6-secondary butyl quinoline); isobornyl acetate; isobornyl methylether; isoeugenol; isolongifolene; jasmine; jojoba; juniper berry; lavender; lavandin; lemon grass; lemon; lime; limonene; linallol oxide; linallol; linalool; linalyl acetate; linseed; *litsea cubeba*; I-methyl acetate; longifolene; mandarin; mentha; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; mineral; mint; musk ambrette; musk ketone; musk xylol; mustard (also known as allylisothio-cyanate); myrcene; nerol; neryl acetate; nonyl aldehyde; nutmeg (e.g., *myristica fragrans*); orange (e.g., *citrus aurantium dulcis*); orris (e.g., *iris florentina*) root; para-cymene; para-hydroxy phenyl butanone crystals (e.g., 4-(4-hydroxphenyl)-2-butanone); passion palmarosa oil (e.g., *cymbopogon martini*); patchouli (e.g., *pogostemon cablin*); p-cymene; pennyroyal oil; pepper; peppermint (e.g., *mentha piperita*); perillaldehyde; petitgrain (e.g., *citrus aurantium amara*); phenyl ethyl alcohol; phenyl ethyl propionate; phenyl ethyl-2-methylbutyrate; pimento berry; pimento leaf; pinane hydroperoxide; pinanol; pine ester; pine needle; pine; pinene; piperonal; piperonyl acetate; piperonyl alcohol; plinol; plinyl acetate; pseudo ionone; rhodinol; rhodinyl acetate; rosalin; rose; rosemary (e.g., *rosmarinus officinalis*); ryu; sage; sandalwood (e.g., *santalum album*); sandenol; sassafras; sesame; soybean; spearmint; spice; spike lavender; spirantol; starflower; tangerine; tea seed; tea tree; terpenoid; terpineol; terpinolene; terpinyl acetate; tert-butylcyclohexyl acetate; tetrahydrolinalool; tetrahydrolinalyl acetate; tetrahydromyrcenol; thulasi; thyme; thymol; tomato; trans-2-hexenol; trans-anethole and metabolites thereof; turmeric; turpentine; vanillin (e.g., 4-hydroxy-3-methoxy benzaldehyde); vetiver; vitalizair; white cedar; white grapefruit; wintergreen (methyl salicylate) and the like.

Further examples of suitable essential oils or their constituents may include, but are not limited to, members selected from the group consisting of aldehyde C16 (pure), α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, dimethyl salicylate, eucalyptol (cineole), eugenol, isoeugenol, galaxolide, geraniol, guaiacol, ionone, d-limonene, menthol, methyl anthranilate, methyl ionone, methyl salicylate, α-phellandrene, pennyroyal oil, perillaldehyde, 1- or 2 phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil (white and red), thymol, trans-anethole, vanillin, ethyl vanillin, and the like.

Use of pesticides is regulated in the United States by the Environmental Protection Agency (EPA) under authority of the Federal Insecticide, Fungicide and Rodenticide Act (FIFRA). Tolerance for residues of pesticides in agricultural commodities are established by the (EPA) and enforced by the Food and Drug Administration (FDA) under authority of the Federal Food, Drug and Cosmetic Act (FD&C Act). This regulatory environment leads to another aspect of this invention, which is an article of manufacture or pest control kit. In this aspect a pest control composition disclosed herein is sold in a container or kit that will be suitable for storing the composition for its shelf life. Associated with the container or kit is printed instructions and/or a printed label providing instructions for using the pest control composition disclosed herein for purposes in accordance with the methods and uses disclosed herein. The container or kit may have associated with it a delivery device that allows the composition to be applied to the pest population or to the area to be treated. For liquid compositions this is generally a hand-operated, motorized or pressurized pressure-driven sprayer. The container or kit may be made of any suitable material such as a polymer, glass, metal, or the like. Usually, the labeling is associated with the container or kit by being adhered to the container or kit, placed inside the container or kit, or otherwise accompanying the container or kit in a package sold to the user. Such label may indicate that the composition is approved for use as a pest control composition. The instructions will spell out the type of pests for which the pest control composition disclosed herein is to be used, the application method, the rate of application, dilution requirements, use precautions, and the like.

A pest control composition disclosed herein has minimal adverse effects on humans, mammals including domestic animals, plant life and the environment. In an aspect of this embodiment, a pest control composition disclosed herein is substantially non-toxic to humans, mammals, plants and the environment. In other aspects of this embodiment, a pest control composition disclosed herein is essentially non-toxic to humans, mammals, plants and the environment.

Aspects of the present specification disclose, in part, a pest control composition that is biodegradable. A biodegradable pest control composition disclosed herein is one that is prone to degrading, eroding, resorbing, decomposing, or breaking down to a substantial or significant degree once applied according to the methods and uses disclosed herein. In aspects of this embodiment, at least 75%, at least 80%, at least 85%, at least 90%, at least 95%, at least 99% of a pest control composition disclosed herein biodegrades in, e.g., about 1 day, about 2 days, about 3 days, about 4 days, about 5 days, about 6 days or about 7 days. In other aspects of this embodiment, at least 75%, at least 80%, at least 85%, at least 90%, at least 95%, at least 99% of a pest control composition disclosed herein biodegrades in, e.g., about 1 to about 2 days, about 1 to about 3 days, about 1 to about 4 days, about 1 to about 5 days, about 1 to about 6 days, about 1 to about 7 days, about 2 to about 3 days, about 2 to about 4 days, about 2 to about 5 days, about 2 to about 6 days, about 2 to about 7 days, about 3 to about 4 days, about 3 to about 5 days, about 3 to about 6 days, about 3 to about 7 days, about 4 to about 5 days, about 4 to about 6 days, about 4 to about 7 days, about 5 to about 6 days, about 5 to about 7 days or about 6 to about 7 days.

In aspects of this embodiment, at least 75%, at least 80%, at least 85%, at least 90%, at least 95%, at least 99% of a pest control composition disclosed herein biodegrades in, e.g., about 7 day, about 8 days, about 9 days, about 10 days, about 11 days, about 12 days, about 13 days or about 14 days. In other aspects of this embodiment, at least 75%, at least 80%, at least 85%, at least 90%, at least 95%, at least 99% of a pest control composition disclosed herein biodegrades in, e.g., about 7 to about 8 days, about 7 to about 9 days, about 7 to about 10 days, about 7 to about 11 days, about 7 to about 12 days, about 7 to about 13 days, about 7 to about 14 days, about 8 to about 9 days, about 8 to about 10 days, about 8 to about 11 days, about 8 to about 12 days, about 8 to about 13 days, about 8 to about 14 days, about 9 to about 10 days, about 9 to about 11 days, about 9 to about 12 days, about 9 to about 13 days, about 9 to about 14 days, about 9 to about 11 days, about 9 to about 12 days, about 9 to about 13 days, about 9 to about 14 days, about 10 to about 11 days, about 10 to about 12 days, about 10 to about 13 days, about 10 to about 14 days, about 11 to about 12 days, about 11 to about 13 days, about 11 to about 14 days, about 12 to about 13 days, about 12 to about 14 days or about 13 to about 14 days.

In aspects of this embodiment, at least 75%, at least 80%, at least 85%, at least 90%, at least 95%, at least 99% of a pest control composition disclosed herein biodegrades in, e.g., about 15 day, about 16 days, about 17 days, about 18 days, about 19 days, about 20 days or about 21 days. In other aspects of this embodiment, at least 75%, at least 80%, at least 85%, at least 90%, at least 95%, at least 99% of a pest control composition disclosed herein biodegrades in, e.g., about 15 to about 16 days, about 15 to about 17 days, about 15 to about 18 days, about 15 to about 19 days, about 15 to about 20 days, about 15 to about 21 days, about 16 to about 17 days, about 16 to about 18 days, about 16 to about 19 days, about 16 to about 20 days, about 16 to about 21 days, about 17 to about 18 days, about 17 to about 19 days, about 17 to about 20 days, about 17 to about 21 days, about 18 to about 19 days, about 18 to about 20 days, about 18 to about 21 days, about 19 to about 20 days, about 19 to about 21 days or about 20 to about 21 days.

Aspects of the present specification disclose, in part, kits comprising one or more components useful to practice a method or use disclosed herein. Kits provide a convenient enclosure of components useful to practice a method or use disclosed herein to facilitate or enhance a commercial sale. For example, a kit may comprises a pest control composition disclosed herein and one or more other reagents useful to practice a method or use disclosed herein, such as, e.g., one or more dilutants and/or one or more carriers.

Kits typically provide a suitable container, e.g., a box or other enclosed carrier that contain the one or more components useful to practice a method or use disclosed herein. In addition, kits disclosed herein will typically include separate containers, e.g., a bottle, a vial, a flask or other enclosed carrier that contains the one or more components. For example, a container for a pest control composition disclosed herein, and a separate container for the one or more other reagents included in the kit. Kits can be portable, for example, able to be transported and used in remote areas such as commercial or industrial installations or agricultural fields. Other kits may be of use in a residential building.

A kit disclosed herein may include labels or inserts. Labels or inserts include "printed matter" that can be provided as separate material, a packing material (e.g., a box), or attached or affixed to a container containing a kit component. Labels or inserts can additionally include a computer readable medium, such as a disk (e.g., hard disk, flash memory), optical disk such as CD- or DVD-ROM/RAM, DVD, MP3, magnetic tape, or an electrical storage media such as RAM and ROM or hybrids of these such as magnetic/optical storage media, FLASH media or memory type cards. Labels or inserts may include identifying information of one or more components therein, dose amounts, does frequency or timing, information on the individual components. Labels or inserts can include information identifying manufacturer information, lot numbers, manufacturer location and date. Labels or inserts can include information on a condition or situation for which a kit component may be used. Labels or inserts can include instructions for using one or more of the kit components in a method, or use as disclosed herein. Instructions can include dosage amounts, frequency or duration, and instructions for practicing any of the methods or uses, or treatment protocols described herein as well as warnings on potential hazards or situations where it would not be appropriate to use the components of the kit.

Aspects of the present specification disclose, in part, a method of controlling a population of invertebrate pests. A method of controlling a population of invertebrate pests disclosed herein includes a step of applying an effective amount of a pest control composition disclosed herein to one or more invertebrate pests and/or applying an effective amount of a pest control composition disclosed herein to one or more locations where invertebrate pest control is desired.

Aspects of the present specification disclose, in part, use of a pest control composition disclosed herein in controlling a population of invertebrate pests. Use of a pest control composition disclosed herein includes applying an effective amount of a pest control composition disclosed herein to one or more invertebrate pests and/or applying an effective amount of a pest control composition disclosed herein to one or more locations where invertebrate pest control is desired.

The combination of the nonionic surfactant and the treated fermented microbial supernatant in the pest control compositions disclosed herein results in an accelerated in situ chemical reactions of the molecular structures, particularly chemical bonds present in polysaccharide and lipid-based components, present in the cuticle, particularly lipid-based components, thereby dissolving, dispersing, or otherwise disrupting one or more components of the cuticle, resulting in their death of the pest through rapid dehydration or desiccation.

Without wishing to be limited by any theory, upon application of a pest control composition in an aqueous environment, highly reactive, uniquely structured, ultra-fine microbubbles are spontaneously formed. These "functionalized" microbubbles comprise an outer "highly reactive" shell composed of one or more nonionic surfactants and components from the treated fermented microbial supernatant and an inner core containing air. The "highly reactive" shell enables a dramatic increase in the mass transfer of oxygen in an aqueous environment and an accelerated bio-catalysis of the molecular structures of compounds, which in combination provide a synergistic functionality. With respect to mass transfer of oxygen, this functionality increases transfer rates of oxygen and raises the level of dissolved oxygen in an aqueous environment which far exceeding the solubility limits anticipated by Henry's Law, and, are at levels that simply cannot be achieved through mechanical aeration systems. It appears that components from the treated fermented microbial supernatant interfere with the ability of the nonionic surfactants to create a well-organized micellar shell. The result is a loose molecular packing of these fermentation components and surfactants that "functionalized" the shell to be more gas permeable, thereby creating more favorable conditions for mass gas transfer. As such, this oxygen transfer function increases the availability of oxygen in an aqueous environment. With respect to accelerated bio-catalysis, this functionality lowers the transition of energy required for a catalytic reaction to occur by providing a reaction platform that increases localized concentrations of reactants, enables donation of electrons and facilitate chemical reactions at electron poor sites. As such, this bio-catalysis function mediates cleavage of chemical bonds, including glycosidic and ester bonds, present in a compound. As such, the "functionalized" shell of the microbubbles have catalytic activities that like conventional enzyme systems, but without the need of any enzymes. Thus, application of a pest control composition disclosed herein creates "functionalized: microbubbles that increase oxygen dispersion resulting in higher dissolved oxygen levels and accelerate molecular interactions resulting in catalytic breakdown of compounds.

When in contact with a cuticle, the "functionalized" shell chemically interacts with lipid-based components of the cuticle in a manner that enables the cleavage of ester bonds present in the lipid-based components. This interaction appears to be a form of hydrolysis using beta-oxidation where, in addition to relying on components of the "functionalized" shell, oxygen present in the core of the microbubble is also utilized. Thus, the lipid-interacting properties present in the "functionalized" shell works synergistically with the oxygen transfer capabilities of the core to enhance the in situ breaking of ester bonds present in lipid-based components.

Application of a pest control composition disclosed herein can be by any method that exposes the pest to the disclosed pest control compositions in a manner that provides adequate disruption of one or more components of the cuticle and subsequent dehydration or desiccation of the pest. For example, exposure can be by direct application to the pest or by indirect application to a location were pest control is desired.

An undiluted form of the pest control composition disclosed herein can be used in the methods and uses disclosed herein. Alternatively, it may desirable to dilute the pest control composition disclosed herein, and those skilled in the art are aware that dilutions of such compositions can be used. Dilution of a pest control composition disclosed herein is typically done using water, although other appropriate diluents may be used so long as they are compatible with the formation of microbubbles as disclosed herein. In aspects of this embodiment, a pest control composition is diluted to a ratio of, e.g., 1:10, 1:25, 1:50, 1:75, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, 1:20000, 1:30000, 1:40000, 1:50000, 1:60000, 1:70000, 1:80000, 1:90000 or 1:100000. In other aspects of this embodiment, a pest control composition is diluted to a ratio of, e.g., at least 1:10, at least 1:25, at least 1:50, at least 1:75, at least 1:100, at least 1:200, at least 1:300, at least 1:400, at least 1:500, at least 1:600, at least 1:700, at least 1:800, at least 1:900, at least 1:1000, at least 1:2000, at least 1:3000, at least 1:4000, at least 1:5000, at least 1:6000, at least 1:7000, at least 1:8000, at least 1:9000, at least 1:10000, at least 1:20000, at least 1:30000, at least 1:40000, at least 1:50000, at least 1:60000, at least 1:70000, at least 1:80000, at least 1:90000 or at least 1:100000. In yet other aspects of this embodiment, a pest control composition is diluted to a ratio of, e.g., at most 1:10, at most 1:25, at most 1:50, at most 1:75, at most 1:100, at most 1:200, at most 1:300, at most 1:400, at most 1:500, at most 1:600, at most 1:700, at most 1:800, at most 1:900, at most 1:1000, at most 1:2000, at most 1:3000, at most 1:4000, at most 1:5000, at most 1:6000, at most 1:7000, at most 1:8000, at most 1:9000, at most 1:10000, at most 1:20000, at most 1:30000, at most 1:40000, at most 1:50000, at most 1:60000, at most 1:70000, at most 1:80000, at most 1:90000 or at most 1:100000.

In still other aspects of this embodiment, a pest control composition is diluted to a ratio of, e.g., about 1:1 to about 1:10, about 1:1 to about 1:25, about 1:1 to about 1:50, about 1:1 to about 1:75, about 1:1 to about 1:100, about 1:2 to about 1:10, about 1:2 to about 1:25, about 1:2 to about 1:50, about 1:2 to about 1:75, about 1:2 to about 1:100, about 1:10 to about 1:25, about 1:10 to about 1:50, about 1:10 to about 1:75, about 1:10 to about 1:100, about 1:10 to about 1:125, about 1:10 to about 1:150, about 1:10 to about 1:175, about 1:10 to about 1:200, about 1:10 to about 1:225, about 1:10 to about 1:250, about 1:50 to about 1:100, about 1:50 to about 1:200, about 1:50 to about 1:300, about 1:50 to about 1:400, about 1:50 to about 1:500, about 1:50 to about 1:600, about 1:50 to about 1:700, about 1:50 to about 1:800, about 1:50 to about 1:900, about 1:50 to about 1:1000, about 1:100 to about 1:200, about 1:100 to about 1:300, about 1:100 to about 1:400, about 1:100 to about 1:500, about 1:100 to about 1:600, about 1:100 to about 1:700, about 1:100 to about 1:800, about 1:100 to about 1:900, about 1:100 to about 1:1000, about 1:500 to about 1:1000, about 1:500 to about 1:2000, about 1:500 to about 1:3000, about 1:500 to about 1:4000, about 1:500 to about 1:5000, about 1:500 to about 1:6000, about 1:500 to about 1:7000, about 1:500 to about 1:8000, about 1:500 to about 1:9000, about 1:500 to about 1:10000, about 1:1000 to about 1:2000, about 1:1000 to about 1:3000, about 1:1000 to about 1:4000, about 1:1000 to about 1:5000, about 1:1000 to about 1:6000, about 1:1000 to about 1:7000, about 1:1000 to about 1:8000, about 1:1000 to about 1:9000, about 1:1000 to about 1:10000, about 1:5000 to about 1:10000, about 1:5000 to about 1:20000, about 1:5000 to about 1:30000, about 1:5000 to about 1:40000, about 1:5000 to about 1:50000, about 1:5000 to about 1:60000, about 1:5000 to about 1:70000, about 1:5000 to about 1:80000, about 1:5000 to about 1:90000, about 1:5000 to about 1:100000, about 1:10000 to about 1:20000, about 1:10000 to about 1:30000, about 1:10000 to about 1:40000, about 1:10000 to about 1:50000, about 1:10000 to about 1:60000, about 1:10000 to about 1:70000, about 1:10000 to about 1:80000, about 1:10000 to about 1:90000, about 1:10000 to about 1:100000.

Application of a pest control composition disclosed herein is in an effective amount. An effective amount of a disclosed pest control composition can be an amount sufficient to cause an adverse effect on the population of a pest sought to be controlled. The actual effective amount of a disclosed pest control composition is determined by routine screening procedures employed to evaluate controlling activity and efficacy of a pest control composition disclosed herein. Such screening procedures are well known by those skilled in the art. It is expected that a pest control composition disclosed herein having a higher level of activity can be used in smaller amounts and concentrations, while those having a lower level of activity may require larger amounts or concentrations in order to achieve the same controlling effect.

In aspects of this embodiment, an effective amount of a disclosed pest control composition is an amount sufficient to cause an adverse effect on, e.g., about 10%, about 15%, about 20%, about 25%, about 30%, about 35%, about 40%, about 45%, about 50%, about 55%, about 60%, about 65%, about 70%, about 75%, about 80%, about 85%, about 90% or about 95% of the pests in the population. In other aspects of this embodiment, an effective amount of a disclosed pest control composition is an amount sufficient to cause an adverse effect on, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% of the pests in the population. In still other aspects of this embodiment, an effective amount of a disclosed pest control composition is an amount sufficient to cause an adverse effect on, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90% or at most 95% of the pests in the population. In yet other aspects of this embodiment, an effective amount of a disclosed pest control composition is an amount that has an adverse effect on, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95% or about 90% to about 95% of the pests in the population.

An effective amount of a disclosed pest control composition can be an amount sufficient to cause mortality to pests sought to be controlled. In aspects of this embodiment, an effective amount of a disclosed pest control composition is an amount sufficient to cause mortality on, e.g., about 10%, about 15%, about 20%, about 25%, about 30%, about 35%, about 40%, about 45%, about 50%, about 55%, about 60%, about 65%, about 70%, about 75%, about 80%, about 85%, about 90% or about 95% of the pests in the population. In other aspects of this embodiment, an effective amount of a disclosed pest control composition is an amount sufficient to cause mortality on, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% of the pests in the population. In yet other aspects of this embodiment, an effective amount of a disclosed pest control composition is an amount sufficient to cause mortality on, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90% or at most 95% of the pests in the population. In still other aspects of this embodiment, an effective amount of a disclosed pest control composition is an amount sufficient to cause mortality on, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95% or about 90% to about 95% of the pests in the population.

An effective amount of a disclosed pest control composition can be an amount sufficient to reduce the size of the population of the pests sought to be controlled. In aspects of this embodiment, an effective amount of a disclosed pest control composition is an amount sufficient to reduce the size of the population of the pests sought to be controlled by, e.g., about 10%, about 15%, about 20%, about 25%, about 30%, about 35%, about 40%, about 45%, about 50%, about 55%, about 60%, about 65%, about 70%, about 75%, about 80%, about 85%, about 90% or about 95%. In other aspects of this embodiment, an effective amount of a disclosed pest control composition is an amount sufficient to reduce the size of the population of the pests sought to be controlled by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, an effective amount of a disclosed pest control composition is an amount sufficient to reduce the size of the population of the pests sought to be controlled by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90% or at most 95%. In still other aspects of this embodiment, an effective amount of a disclosed pest control composition is an amount sufficient to reduce the size of the population of the pests sought to be controlled by, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95% or about 90% to about 95%.

An effective amount of a disclosed pest control composition can be an amount sufficient to deter pests sought to be controlled from entering or infesting one or more locations.

In aspects of this embodiment, an effective amount of a disclosed pest control composition is an amount sufficient to deter, e.g., about 10%, about 15%, about 20%, about 25%, about 30%, about 35%, about 40%, about 45%, about 50%, about 55%, about 60%, about 65%, about 70%, about 75%, about 80%, about 85%, about 90% or about 95% of the pests in the population from entering or infesting one or more locations. In other aspects of this embodiment, an effective amount of a disclosed pest control composition is an amount sufficient to deter, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% of the pests in the population from entering or infesting one or more locations. In yet other aspects of this embodiment, an effective amount of a disclosed pest control composition is an amount sufficient to deter, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90% or at most 95% of the pests in the population from entering or infesting one or more locations. In still other aspects of this embodiment, an effective amount of a disclosed pest control composition is an amount sufficient to deter, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95% or about 90% to about 95% of the pests in the population from entering or infesting one or more locations.

An effective amount of a disclosed pest control composition can be a dilution of a pest control composition disclosed herein. In aspects of this embodiment, an effective amount of a disclosed pest control composition is a pest control composition:dilutant ratio of, e.g., about 1:50, about 1:75, about 1:100, about 1:125, about 1:150, about 1:175, about 1:200, about 1:225, about 1:250, about 1:275, about 1:300, about 1:325, about 1:350, about 1:375, about 1:400, about 1:425, about 1:450, about 1:475, about 1:500, about 1:525, about 1:550, about 1:575 or about 1:600. In other aspects of this embodiment, an effective amount of a disclosed pest control composition is a pest control composition:dilutant ratio of, e.g., at least 1:50, at least 1:75, at least 1:100, at least 1:125, at least 1:150, at least 1:175, at least 1:200, at least 1:225, at least 1:250, at least 1:275, at least 1:300, at least 1:325, at least 1:350, at least 1:375, at least 1:400, at least 1:425, at least 1:450, at least 1:475, at least 1:500, at least 1:525, at least 1:550, at least 1:575 or at least 1:600. In yet other aspects of this embodiment, an effective amount of a disclosed pest control composition is a pest control composition:dilutant ratio of, e.g., at most 1:50, at most 1:75, at most 1:100, at most 1:125, at most 1:150, at most 1:175, at most 1:200, at most 1:225, at most 1:250, at most 1:275, at most 1:300, at most 1:325, at most 1:350, at most 1:375, at most 1:400, at most 1:425, at most 1:450, at most 1:475, at most 1:500, at most 1:525, at most 1:550, at most 1:575 or at most 1:600. In other aspects of this embodiment, an effective amount of a disclosed pest control composition is a pest control composition:dilutant ratio of, e.g., about 1:50 to about 1:100, about 1:50 to about 1:200, about 1:50 to about 1:300, about 1:50 to about 1:400, about 1:50 to about 1:500, about 1:50 to about 1:600, about 1:100 to about 1:200, about 1:100 to about 1:300, about 1:100 to about 1:400, about 1:100 to about 1:500, about 1:100 to about 1:600, about 1:200 to about 1:300, about 1:200 to about 1:400, about 1:200 to about 1:500, about 1:200 to about 1:600, about 1:300 to about 1:400, about 1:300 to about 1:500, about 1:300 to about 1:600, about 1:400 to about 1:500, about 1:400 to about 1:600 or about 1:500 to about 1:600.

In aspects of this embodiment, an effective amount of a disclosed pest control composition is a pest control composition:dilutant ratio of, e.g., about 1:500, about 1:750, about 1:1000, about 1:1250, about 1:1500, about 1:1750, about 1:2000, about 1:2250, about 1:2500, about 1:2750, about 1:3000, about 1:3250, about 1:3500, about 1:3750, about 1:4000, about 1:4250, about 1:4500, about 1:4750, about 1:5000, about 1:5250, about 1:5500, about 1:5750, about 1:6000 about 1:7000, about 1:8000, about 1:9000 or about 1:10000. In other aspects of this embodiment, an effective amount of a disclosed pest control composition is a pest control composition:dilutant ratio of, e.g., at least 1:500, at least 1:750, at least 1:1000, at least 1:1250, at least 1:1500, at least 1:1750, at least 1:2000, at least 1:2250, at least 1:2500, at least 1:2750, at least 1:3000, at least 1:3250, at least 1:3500, at least 1:3750, at least 1:4000, at least 1:4250, at least 1:4500, at least 1:4750, at least 1:5000, at least 1:5250, at least 1:5500, at least 1:5750, at least 1:6000, at least 1:7000, at least 1:8000, at least 1:9000 or at least 1:10000. In yet other aspects of this embodiment, an effective amount of a disclosed pest control composition is a pest control composition:dilutant ratio of, e.g., at most 1:500, at most 1:750, at most 1:1000, at most 1:1250, at most 1:1500, at most 1:1750, at most 1:2000, at most 1:2250, at most 1:2500, at most 1:2750, at most 1:3000, at most 1:3250, at most 1:3500, at most 1:3750, at most 1:4000, at most 1:4250, at most 1:4500, at most 1:4750, at most 1:5000, at most 1:5250, at most 1:5500, at most 1:5750, at most 1:6000 at most 1:7000, at most 1:8000, at most 1:9000 or at most 1:10000. In other aspects of this embodiment, an effective amount of a disclosed pest control composition is a pest control composition:dilutant ratio of, e.g., about 1:500 to about 1:1000, about 1:500 to about 1:2000, about 1:500 to about 1:3000, about 1:500 to about 1:4000, about 1:500 to about 1:5000, about 1:500 to about 1:6000, about 1:500 to about 1:7000, about 1:500 to about 1:8000, about 1:500 to about 1:9000, about 1:500 to about 1:10000, about 1:1000 to about 1:2000, about 1:1000 to about 1:3000, about 1:1000 to about 1:4000, about 1:1000 to about 1:5000, about 1:1000 to about 1:6000, about 1:1000 to about 1:7000, about 1:1000 to about 1:8000, about 1:1000 to about 1:9000, about 1:1000 to about 1:10000, about 1:2000 to about 1:3000, about 1:2000 to about 1:4000, about 1:2000 to about 1:5000, about 1:2000 to about 1:6000, about 1:2000 to about 1:7000, about 1:2000 to about 1:8000, about 1:2000 to about 1:9000, about 1:2000 to about 1:10000, about 1:3000 to about 1:4000, about 1:3000 to about 1:5000, about 1:3000 to about 1:6000, about 1:3000 to about 1:7000, about 1:3000 to about 1:8000, about 1:3000 to about 1:9000, about 1:3000 to about 1:10000, about 1:4000 to about 1:5000, about 1:4000 to about 1:6000, about 1:4000 to about 1:7000, about 1:4000 to about 1:8000, about 1:4000 to about 1:9000, about 1:4000 to about 1:10000, about 1:5000 to about 1:6000, about 1:5000 to about 1:7000, about 1:5000 to about 1:8000, about 1:5000 to about 1:9000, about 1:5000 to about 1:10000, about 1:6000 to about 1:7000, about 1:6000 to about 1:8000, about 1:6000 to about 1:9000, about 1:6000 to about 1:10000, about 1:7000 to about 1:8000, about 1:7000 to about 1:9000, about 1:7000 to about 1:10000, about 1:8000 to about 1:9000, about 1:8000 to about 1:10000 or about 1:9000 to about 1:10000.

In aspects of this embodiment, an effective amount of a disclosed pest control composition has a final concentration of, e.g., about 0.0001%, about 0.0002%, about 0.0003%, about 0.0004%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9% or about 10%. In other aspects of this embodiment, an effective amount of a disclosed pest control composition has a final concentration of, e.g., at least 0.0001%, at least 0.0002%, at least 0.0003%, at least 0.0004%, at least 0.0005%, at least 0.0006%, at least 0.0007%, at least 0.0008%, at least 0.0009%, at least 0.001%, at least 0.002%, at least 0.003%, at least 0.004%, at least 0.005%, at least 0.006%, at least 0.007%, at least 0.008%, at least 0.009%, at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9% or at least 10%. In yet other aspects of this embodiment, an effective amount of a disclosed pest control composition has a final concentration of, e.g., at most 0.0001%, at most 0.0002%, at most 0.0003%, at most 0.0004%, at most 0.0005%, at most 0.0006%, at most 0.0007%, at most 0.0008%, at most 0.0009%, at most 0.001%, at most 0.002%, at most 0.003%, at most 0.004%, at most 0.005%, at most 0.006%, at most 0.007%, at most 0.008%, at most 0.009%, at most 0.01%, at most 0.02%, at most 0.03%, at most 0.04%, at most 0.05%, at most 0.06%, at most 0.07%, at most 0.08%, at most 0.09%, at most 0.1%, at most 0.2%, at most 0.3%, at most 0.4%, at most 0.5%, at most 0.6%, at most 0.7%, at most 0.8%, at most 0.9%, at most 1%, at most 2%, at most 3%, at most 4%, at most 5%, at most 6%, at most 7%, at most 8%, at most 9% or at most 10%. In still other aspects of this embodiment, an effective amount of a disclosed pest control composition has a final concentration of, e.g., about 0.0001% to about 0.0005%, about 0.0001% to about 0.001%, about 0.0001% to about 0.005%, about 0.0001% to about 0.01%, about 0.0001% to about 0.05%, about 0.0001% to about 0.1%, about 0.0001% to about 0.5%, about 0.0001% to about 1%, about 0.0001% to about 5%, about 0.0001% to about 10%, about 0.0005% to about 0.001%, about 0.0005% to about 0.005%, about 0.0005% to about 0.01%, about 0.0005% to about 0.05%, about 0.0005% to about 0.1%, about 0.0005% to about 0.5%, about 0.0005% to about 1%, about 0.0005% to about 5%, about 0.0005% to about 10%, about 0.001% to about 0.005%, about 0.001% to about 0.01%, 0.001% to about 0.05%, about 0.001% to about 0.1%, 0.001% to about 0.5%, 0.001% to about 1%, 0.001% to about 5%, about 0.001% to about 10%, about 0.005% to about 0.01%, about 0.005% to about 0.05%, about 0.005% to about 0.1%, about 0.005% to about 0.5%, about 0.005% to about 1%, about 0.005% to about 5%, about 0.005% to about 10%, about 0.01% to about 0.05%, about 0.01% to about 0.1%, about 0.01% to about 0.5%, about 0.01% to about 1%, about 0.01% to about 5%, about 0.01% to about 10%, about 0.05% to about 0.1%, about 0.05% to about 0.5%, about 0.05% to about 1%, about 0.05% to about 5%, about 0.05% to about 10%, about 0.1% to about 0.5%, about 0.1% to about 1%, about 0.1% to about 5%, about 0.1% to about 10%, about 0.5% to about 1%, about 0.5% to about 5%, about 0.5% to about 10%, about 1% to about 5%, about 1% to about 10% or about 5% to about 10%.

The efficacy of the pest control composition disclosed herein may be monitored by determining the adverse effect, mortality, reduced pest population, reduced entering or infestation of one or more locations, or any other assessment of damage to a pest population, including, without limitation, inhibition, arrestment, or retardation of pest growth, inhibition, arrestment, or retardation of pest reproduction or inhibition, arrestment, or retardation of pest development, all of which are encompassed by the term "controlling". Efficacy is also monitored by phytotoxicity to the plants that are infested with the pest population, tissue damage to the host infected with the pest population and any adverse effects that might be experienced by a human who is applying a disclosed pest control composition to an infested plant or animal, or otherwise exposed to a pest control composition disclosed herein. Accordingly, the amount of a pest control composition disclosed herein used in the disclosed methods or uses, meets the effective amount criteria above, and preferably has minimal or no adverse effect on ornamental and agricultural plants (such as phytotoxicity), wildlife and humans that may come into contact with such compositions.

Application of a pest control composition disclosed herein can be achieved by any process that effectively creates microbubbles as disclosed herein and effectively exposes the pests sought to be controlled. For example any method that can introduce large concentrations of a gas into the pest control composition during application is suitable because such gas introduction enables the spontaneous formation of microbubbles. Suitable application processes include, without limitation, spraying, fogging, atomizing, vaporizing, scattering, watering, squirting, sprinkling and the like. One preferred method of application is by a manual or mechanical application by irrigation, spraying, fogging, atomizing or vaporizing. Such applications provide formation of finely divided mist with sufficient aeration during the application process to create microbubbles as disclosed herein. Microbubbles exposed to a dispersion of gas in a liquid show colloidal properties and are referred to as colloidal gas aphrons (CGA). CGA differ from ordinary gas bubbles in that they contain a distinctive shell layer containing a low concentration of a surfactant.

The microbubbles formed with the pest control composition disclosed herein appear to increase the mass transfer of oxygen in liquids. Without being bound by scientific theory, there are several possible explanations for this difference. First, the surfactants formulated into a pest control composition disclosed herein include nonionic surfactants and/or biosurfactants which significantly alter the properties of bubble behavior. Second, a pest control composition disclosed herein requires a much lower concentration of surfactants for microbubble formation. It has been suggested that surfactant concentrations must approach the critical micelles concentration (CMS) of a surfactant system. In a pest control composition disclosed herein, microbubbles are formed below estimated CMCs for the surfactants used. This suggests that the microbubbles are the result of aggregates of surfactant molecules with a loose molecular packing more favorable to gas mass transfer characteristics. A surface containing fewer surfactant molecules would be more gas permeable than a well-organized micelle containing gas. Regardless of the mechanism, the tendency of a pest control composition disclosed herein to organizes into clusters, aggregates, or gas-filled bubbles provides a platform for reactions to occur by increasing localized concentrations of reactants, lowering the transition of energy required for a catalytic reaction to occur, or some other mechanism which has not yet been described.

In aspects of this embodiment, a microbubbles disclosed herein have a mean diameter of, e.g., about 5 μm, about 10 μm, about 15 μm, about 20 μm, about 25 μm, about 30 μm, about 40 μm, about 50 μm, about 75 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm or about 1000 μm. In other aspects of this embodiment, a microbubbles disclosed herein have a mean diameter of, e.g., at least 5 μm, at least 10 μm, at least 15 μm, at least 20 μm, at least 25 μm, at least 30 μm, at least 40 μm, at least 50 μm, at least 100 μm, at least 150 μm, at least 200 μm, at least 250 μm, at least 300 μm, at least 350 μm, at least 400 μm, at least 450 μm, at least 500 μm, at least 550 μm, at least 600 μm, at least 650 μm, at least 700 μm, at least 750 μm, at least 800 μm, at least 850 μm, at least 900 μm, at least 950 μm or at least 1000 μm. In other aspects of this embodiment, a microbubbles disclosed herein have a mean diameter of, e.g., at most 5 μm, at most 10 μm, at most 15 μm, at most 20 μm, at most 25 μm, at most 30 μm, at most 40 μm, at most 50 μm, at most 100 μm, at most 150 μm, at most 200 μm, at most 250 μm, at most 300 μm, at most 350 μm, at most 400 μm, at most 450 μm, at most 500 μm, at most 550 μm, at most 600 μm, at most 650 μm, at most 700 μm, at most 750 μm, at most 800 μm, at most 850 μm, at most 900 μm, at most 950 μm or at most 1000 μm.

In aspects of this embodiment, a microbubbles disclosed herein have a mean diameter of, e.g., about 5 μm to about 10 μm, about 5 μm to about 15 μm, about 5 μm to about 20 μm, about 5 μm to about 25 μm, about 5 μm to about 30 μm, about 5 μm to about 40 μm, about 5 μm to about 50 μm, about 5 μm to about 75 μm, about 5 μm to about 100 μm, about 10 μm to about 15 μm, about 10 μm to about 20 μm, about 10 μm to about 25 μm, about 10 μm to about 30 μm, about 10 μm to about 40 μm, about 10 μm to about 50 μm, about 10 μm to about 75 μm, about 10 μm to about 100 μm, about 15 μm to about 20 μm, about 15 μm to about 25 μm, about 15 μm to about 30 μm, about 15 μm to about 40 μm, about 15 μm to about 50 μm, about 15 μm to about 75 μm, about 15 μm to about 100 μm, about 20 μm to about 25 μm, about 20 μm to about 30 μm, about 20 μm to about 40 μm, about 20 μm to about 50 μm, about 20 μm to about 75 μm, about 20 μm to about 100 μm, about 25 μm to about 30 μm, about 25 μm to about 40 μm, about 25 μm to about 50 μm, about 25 μm to about 75 μm, about 25 μm to about 100 μm, about 30 μm to about 40 μm, about 30 μm to about 50 μm, about 30 μm to about 75 μm, about 30 μm to about 100 μm, about 40 μm to about 50 μm, about 40 μm to about 75 μm, about 40 μm to about 100 μm, about 50 μm to about 75 μm, about 50 μm to about 100 μm, about 50 μm to about 150 μm, about 50 μm to about 200 μm, about 50 μm to about 250 μm, about 50 μm to about 300 μm, about 50 μm to about 350 μm, about 50 μm to about 400 μm, about 50 μm to about 450 μm, about 50 μm to about 500 μm, about 50 μm to about 550 μm, about 50 μm to about 600 μm, about 50 μm to about 650 μm, about 50 μm to about 700 μm, about 50 μm to about 750 μm, about 50 μm to about 800 μm, about 50 μm to about 850 μm, about 50 μm to about 900 μm, about 50 μm to about 950 μm, about 50 μm to about 1000 μm, about 100 μm to about 150 μm, about 100 μm to about 200 μm, about 100 μm to about 250 μm, about 100 μm to about 300 μm, about 100 μm to about 350 μm, about 100 μm to about 400 μm, about 100 μm to about 450 μm, about 100 μm to about 500 μm, about 100 μm to about 550 μm, about 100 μm to about 600 μm, about 100 μm to about 650 μm, about 100 μm to about 700 μm, about 100 μm to about 750 μm, about 100 μm to about 800 μm, about 100 μm to about 850 μm, about 100 μm to about 900 μm, about 100 μm to about 950 μm, about 100 μm to about 1000 μm, about 150 μm to about 200 μm, about 150 μm to about 250 μm, about 150 μm to about 300 μm, about 150 μm to about 350 μm, about 150 μm to about 400 μm, about 150 μm to about 450 μm, about 150 μm to about 500 μm, about 150 μm to about 550 μm, about 150 μm to about 600 μm, about 150 μm to about 650 μm, about 150 μm to about 700 μm, about 150 μm to about 750 μm, about 150 μm to about 800 μm, about 150 μm to about 850 μm, about 150 μm to about 900 μm, about 150 μm to about 950 μm, about 150 μm to about 1000 μm, about 200 μm to about 250 μm, about 200 μm to about 300 μm, about 200 μm to about 350 μm, about 200 μm to about 400 μm, about 200 μm to about 450 μm, about 200 μm to about 500 μm, about 200 μm to about 550 μm, about 200 μm to about 600 μm, about 200 μm to about 650 μm, about 200 μm to about 700 μm, about 200 μm to about 750 μm, about 200 μm to about 800 μm, about 200 μm to about 850 μm, about 200 μm to about 900 μm, about 200 μm to about 950 μm, about 200 μm to about 1000 μm, about 250 μm to about 300 μm, about 250 μm to about 350 μm, about 250 μm to about 400 μm, about 250 μm to about 450 μm, about 250 μm to about 500 μm, about 250 μm to about 550 μm, about 250 μm to about 600 μm, about 250 μm to about 650 μm, about 250 μm to about 700 μm, about 250 μm to about 750 μm, about 250 μm to about 800 μm, about 250 μm to about 850 μm, about 250 μm to about 900 μm, about 250 μm to about 950 μm, about 250 μm to about 1000 μm, about 300 μm to about 350 μm, about 300 μm to about 400 μm, about 300 μm to about 450 μm, about 300 μm to about 500 μm, about 300 μm to about 550 μm, about 300 μm to about 600 μm, about 300 μm to about 650 μm, about 300 μm to about 700 μm, about 300 μm to about 750 μm, about 300 μm to about 800 μm, about 300 μm to about 850 μm, about 300 μm to about 900 μm, about 300 μm to about 950 μm, about 300 μm to about 1000 μm, about 350 μm to about 400 μm, about 350 μm to about 450 μm, about 350 μm to about 500 μm, about 350 μm to about 550 μm, about 350 μm to about 600 μm, about 350 μm to about 650 μm, about 350 μm to about 700 μm, about 350 μm to about 750 μm, about 350 μm to about 800 μm, about 350 μm to about 850 μm, about 350 μm to about 900 μm, about 350 μm to about 950 μm, about 350 μm to about 1000 μm, about 400 μm to about 450 μm, about 400 μm to about 500 μm, about 400 μm to about 550 μm, about 400 μm to about 600 μm, about 400 μm to about 650 μm, about 400 μm to about 700 μm, about 400 μm to about 750 μm, about 400 μm to about 800 μm, about 400 µm to about 850 µm, about 400 µm to about 900 µm, about 400 µm to about 950 µm, about 400 µm to about 1000 µm, about 450 µm to about 500 µm, about 450 µm to about 550 µm, about 450 µm to about 600 µm, about 450 µm to about 650 µm, about 450 µm to about 700 µm, about 450 µm to about 750 µm, about 450 µm to about 800 µm, about 450 µm to about 850 µm, about 450 µm to about 900 µm, about 450 µm to about 950 µm, about 450 µm to about 1000 µm, about 500 µm to about 550 µm, about 500 µm to about 600 µm, about 500 µm to about 650 µm, about 500 µm to about 700 µm, about 500 µm to about 750 µm, about 500 µm to about 800 µm, about 500 µm to about 850 µm, about 500 µm to about 900 µm, about 500 µm to about 950 µm, about 500 µm to about 1000 µm, about 550 µm to about 600 µm, about 550 µm to about 650 µm, about 550 µm to about 700 µm, about 550 µm to about 750 µm, about 550 µm to about 800 µm, about 550 µm to about 850 µm, about 550 µm to about 900 µm, about 550 µm to about 950 µm, about 550 µm to about 1000 µm, about 600 µm to about 650 µm, about 600 µm to about 700 µm, about 600 µm to about 750 µm, about 600 µm to about 800 µm, about 600 µm to about 850 µm, about 600 µm to about 900 µm, about 600 µm to about 950 µm, about 600 µm to about 1000 µm, about 650 µm to about 700 µm, about 650 µm to about 750 µm, about 650 µm to about 800 µm, about 650 µm to about 850 µm, about 650 µm to about 900 µm, about 650 µm to about 950 µm, about 650 µm to about 1000 µm, about 700 µm to about 750 µm, about 700 µm to about 800 µm, about 700 µm to about 850 µm, about 700 µm to about 900 µm, about 700 µm to about 950 µm, about 700 µm to about 1000 µm, about 750 µm to about 800 µm, about 750 µm to about 850 µm, about 750 µm to about 900 µm, about 750 µm to about 950 µm, about 750 µm to about 1000 µm, about 800 µm to about 850 µm, about 800 µm to about 900 µm, about 800 µm to about 950 µm, about 800 µm to about 1000 µm, about 850 µm to about 900 µm, about 850 µm to about 950 µm, about 850 µm to about 1000 µm, about 900 µm to about 950 µm, about 900 µm to about 1000 µm or about 950 µm to about 1000 µm.

Aspects of the present specification disclose, in part, a location. A location includes, by way of example, a plant or group of plants or part of a plant, a particular area of land like a lawn, a garden or an agricultural field, or a man-made structure, such as, e.g., a commercial building, a residential house, a community facility, a barn, a stable, a shed, a greenhouse or any other physical structure. As used herein, the term "plant" refers to any living organism belonging to the Kingdom Plantae. Non-limiting examples include trees, flowering plant, herbs, bushes, grasses, vines, ferns, mosses, and green algae. As used herein, the term "flower" is synonymous with "bloom" or "blossom" and refers the reproductive structure found in angiosperms. As used herein, the term "crop plant" refers to a plant that produces a crop. Non-limiting examples include are plants that produce fruits, seeds, nuts, grains, oil, wood, and fibers. As used herein, the term "crop" refers to a plant product which is of economic value. Non-limiting examples include are fruits, seeds, nuts, grains, oil, wood, and fibers.

As such, a pest control composition disclosed herein is advantageously employed in a wide variety of locations, including without limitation, household applications, lawn and garden applications, agriculture applications, organic farming applications, greenhouse and nursery applications, stored product applications, professional pest control applications, pet bedding applications, foliage applications, underwater or submerged applications, solid treatment applications, soil incorporation applications, seedling box treatment applications, stalk injection and planting treatment applications.

Invertebrate pests whose population can be controlled by a pest control composition, method and/or use disclosed herein include, without limitation, nematodes, insects and arachnids. In addition, all stages of development can be controlled by a pest control composition, method and/or use disclosed herein include, without limitation, egg, larval, nymphal, juvenile, pupal and adult. Non-limiting examples of invertebrate pests include round worms, cockroaches, ants, flies, spiders, mites, aphids, thrips, whiteflies, loopers, worms, beetles, leafrollers, moths and weevils.

In an embodiment, a pest control composition, method and/or use disclosed herein can control a population of pests belongs to the Phyla Nematoda and/or Arthropoda. In aspects of this embodiment, a pest control composition, method and/or use disclosed herein can control a population of pests belongs to the Subphyla Chelicerata, Myriapoda, and/or Hexapoda. In other aspects of this embodiment, a pest control composition, method and/or use disclosed herein can control a population of pests belongs to the Classes of Arachnida, Symphyla, and/or Insecta.

In another embodiment, a pest control composition, method and/or use disclosed herein can control a population of pests belonging to the Order Anoplura. A non-exhaustive list of particular genera includes, but is not limited to, *Haematopinus, Hoplopleura, Linognathus, Pediculus* and *Polyplax*. A non-exhaustive list of particular species includes, but is not limited to, *Haematopinus asini, Haematopinus suis, Linognathus setosus, Linognathus ovillus, Pediculus humanus capitis, Pediculus humanus*, and *Pthirus pubis*.

In another embodiment, a pest control composition, method and/or use disclosed herein can control a population of pests belonging to the Order Coleoptera (beetles). A non-exhaustive list of particular genera includes, but is not limited to, *Acanthoscelides, Agrilus, Agriotes, Anoplophora, Anthonomus, Aphidius, Apion, Apogonia, Ataenius, Atomaria, Aulacophora, Bothynoderes, Bruchus, Cacoesia, Callosobruchus, Carpophilus, Cerosterna, Cerotoma, Cassida, Cerosterna, Cerotoma, Ceutorhynchus, Chaetocnema, Colaspis, Conoderus, Conotrachelus, Cotinus, Crioceris, Cryptolestes, Ctenicera, Curculio, Cyclocephala, Cylindrocpturus, Deporaus, Dermestes, Diabrotica, Epilachna, Faustinus, Hylobius, Hypera, Hyperdoes, Hypothenemus, Ips, Lasioderma, Leptinotarsa, Liogenys, Lissorhoptrus, Lyctus, Maecolaspis, Megascelis, Melanotus, Meligethes, Melolontha, Oberea, Oryctes, Oryzaephilus, Otiorhynchus, Oulema, Pantomorus, Phyllophaga, Phyllotreta, Phynchites, Popillia, Prostephanus, Rhizopertha, Rhizotrogus, Rhynchites, Rhynchophorus, Scolytus, Shenophorus, Sphenophorus, Sitona, Sitophilus, Stegobium, Tribolium, Trogoderma* and *Zabrus*. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocpturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne,*

*Leptinotarsa decemlineata, Liogenys fuscus, Liogenys suturalis, Lissorhoptrus oryzophilus, Maecolaspis joliveti, Melanotus communis, Meligethes aeneus, Melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile,* and *tenebrioides.*

In another embodiment, a pest control composition, method and/or use disclosed herein can control a population of pests belongs to the Order Dermaptera (earwigs).

In another embodiment, a pest control composition, method and/or use disclosed herein can control a population of pests belongs to the Order Dictyoptera (Blattaria, cockroaches). A non-exhaustive list of particular genera includes, but is not limited to, *Blattella, Parcoblatta, Periplaneta, Pycnoscelus* and *Supella.* A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis* and *Supella longipalpa.*

In another embodiment, a pest control composition, method and/or use disclosed herein can control a population of pests belongs to the Order Diptera (flies). A non-exhaustive list of particular genera includes, but is not limited to, *Aedes, Agromyza, Anastrepha, Anopheles, Bactrocera, Ceratitis, Chrysops, Cochliomyia, Contarinia, Culex, Dasineura, Delia, Drosophila, Fannia, Gasterophilus, Gracillia, Haematobia, Hylemyia, Hypoderma, Liriomyza, Melophagus, Musca, Oestrus, Oscinella, Pegomyia, Phorbia, Psila, Rhagoletis, Sitodiplosis, Stomoxys, Tabanus,* and *Tipula.* A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana,* and *Stomoxys calcitrans.*

In another embodiment, a pest control composition, method and/or use disclosed herein can control a population of pests belongs to the Order Hemiptera (true bugs). A non-exhaustive list of particular genera includes, but is not limited to, *Acrosternum, Adelges, Aulacaspis, Aphrophora, Aphis, Bemisia, Blissus, Calocoris, Ceroplastes, Chionaspis, Chrysomphalus, Cimex, Coccus, Dagbertus, Dichelops, Dysdercus, Edessa, Empoasca, Eurygaster, Euschistus, Helopeltis, Lagynotomus, Lepidosaphes, Leptocorisa, Lygus, Maconellicoccus, Macrosiphum, Nephotettix, Neurocolpus, Nezara, Philaenus, Phytocoris, Piezodorus, Planococcus, Poecilocapsus, Psallus, Pseudacysta, Pseudococcus, Rhopalosiphum, Saissetia, Scaptocoris, Therioaphis, Toumeyella, Toxoptera, Trialeurodes, Triatoma* and *Unaspis.* A non-exhaustive list of particular species includes, but is not limited to, *Acrosternum hilare, Acyrthosiphon pisum, Aleyrodes proletella, Aleurodicus disperses, Aleurothrixus floccosus, Amrasca biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servos, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relatives, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, a pest control composition, method and/or use disclosed herein can control a population of pests belongs to the Order Homoptera. A non-exhaustive list of particular genera includes, but is not limited to, *Acrythosiphon, Adelges, Aleurodes, Aleurodicus, Aleurothrixus, Aluacaspis, Amrasca, Aphrophora, Aonidiella, Aphis, Aulacorthum, Bemisia, Brachycolus, Brachycorynella, Brevennia, Brevicoryne, Ceroplastes, Chionaspis, Chrysomphalus, Coccus, Dysaphis, Empoasca, Eriosoma, Icerya, Idioscopus, Laodelphax, Lepidosaphes, Macrosiphum, Macrosteles, Mahanarva, Metopolophium, Mictis, Myzus, Nephotettix, Nilaparvata, Parlatoria, Peregrinus, Philaenus, Phylloxera, Physokermes, Planococcus, Pseudococcus, Quadraspidiotus, Rhapalosiphum, Saissetia, Schizaphis, Sitobion, Sogatella, Therioaphis, Toumeyella, Toxoptera, Trialeurodes, Unaspis* and *Zulia.* A non-exhaustive list of particular species includes, but is not limited to, *Acrythosiphon pisum, Aleurodes proletella, Aleurodicus disperses, Aleurothrixus floccosus, Amrasca bigutella, Aonidiella aurantii, Aphis gossypii, Aphis pomi, Aulacorthum solani, Bemisia argentifolii, Bemisia tabaci, Brachycolus noxius, Brachycorynella asparagi, Brevennia rehi, Brevicoryne brassicae, Ceroplastes rubens, Dysaphis plantaginea, Eriosoma lanigerum, Icerya purchasi, Idioscopus nitidulus, Laodelphax striatellus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Nilaparvata lugens, Parlatoria pergandii, Parlatoria ziziphi, Peregrinus maidis, Phylloxera vitifoliae, Physokermes piceae, Pseudococcus brevipes, Quadraspidiotus perniciosus, Rhapalosiphum maida, Rhapalosiphum padi, Saissetia oleae, Schizaphis graminum, Sitobion avenae, Sogatella furcifera, Trialeurodes vaporariorum, Trialeurodes abutiloneus, Unaspis yanonensis* and *Zulia entrerriana.*

In another embodiment, a pest control composition, method and/or use disclosed herein can control a population of pests belongs to the Order Hymenoptera. A non-exhaustive list of particular genera includes, but is not limited to, *Acromyrmex, Athalia, Atta, Camponotus, Diprion, Formica, Iridomyrmex, Monomorium, Neodiprion, Pogonomyrmex, Polistes, Solenopsis, Tapoinoma, Tetranomorium, Vespula,* and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile*.

In another embodiment, a pest control composition, method and/or use disclosed herein can control a population of pests belongs to the Order Isoptera. A non-exhaustive list of particular genera includes, but is not limited to, *Coptotermes, Cornitermes, Cryptotermes, Heterotermes, Kalotermes, Incisitermes, Macrotermes, Marginitermes, Microcerotermes, Procornitermes, Reticulitermes, Schedorhinotermes* and *Zootermopsis*. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus*.

In another embodiment, a pest control composition, method and/or use disclosed herein can control a population of pests belongs to the Order Lepidoptera (butterflies). A non-exhaustive list of particular genera includes, but is not limited to, *Achoea, Adoxophyes, Agrotis, Alabama, Amorbia, Amyelosis, Anacamptodes, Anarsia, Anomis, Amorbia, Anticarsia, Archips, Argyrotaenia, Autographa, Bonagota, Borbo, Bucculatrix, Cacoecia, Caloptilia, Capua, Carposina, Chilo, Chlumetia, Choristoneura, Chrysodeixis, Cnaphalocerus, Colias, Conpomorpha, Cossus, Crambus, Cydiafunebrana, Cydia, Darna, Diaphania, Diatraea, Earias, Ecdytopopha, Elasmopalpus, Ephestia, Epimecis, Epinotia, Epiphysias, Erionota, Eupoecilia, Euxoa, Feltia, Gortyna, Grapholita, Hedylepta, Helicoverpa, Heliothis, Hellula, Indarbela, Keiferia, Leucinodes, Leucoptera, Lithocolletis, Lobesia, Loxagrotis, Lymantria, Lyonetia, Mahasena, Malacosoma, Mamestra, Maruca, Metisa, Mythimna, Neoleucinodes, Nymphula, Operophthera, Ostrinia, Oxydia, Pandemis, Papilio, Pectinophora, Peridroma, Perileucoptera, Phthorimaea, Phyllocnisitis, Phyllonorycter, Pseudaletia, Pieris, Plathypena, Plodia, Plutella, Polychrosis, Prays, Pseudaletia, Pseudoplusia, Rachiplusia, Scirpophaga, Sesamia, Setora, Sitotroga, Sparganothis, Spodoptera, Synanthedon, Thecla, Thermisia, Tineol, Trichoplusi, Tuta, Yponomeuta* and *Zeuzera*. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina*.

In another embodiment, a pest control composition, method and/or use disclosed herein can control a population of pests belongs to the Order Mallophaga (chewing lice). A non-exhaustive list of particular genera includes, but is not limited to, *Anaticola, Bovicola, Chelopistes, Goniodes, Menacanthus, Menopon* and *Trichodectes*. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis*.

In another embodiment, a pest control composition, method and/or use disclosed herein can control a population of pests belongs to the Order Orthoptera. A non-exhaustive list of particular genera includes, but is not limited to, *Anabrus, Gryllotalpidae, Locusta, Melanoplus, Microcentrum, Pterophylla, Scudderia* and *Valanga*. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata*.

In another embodiment, a pest control composition, method and/or use disclosed herein can control a population of pests belongs to the Order Phthiraptera (sucking lice). A non-exhaustive list of particular genera includes, but is not limited to, *Haematopinus, Linognathus, Pediculus* and *Pthirus*. A non-exhaustive list of particular species includes, but is not limited to, *Linognathus ovillus, Pediculus humanus capitis, Pediculus humanus,* and *Pthirus pubis*.

In another embodiment, a pest control composition, method and/or use disclosed herein can control a population of pests belongs to the Order Siphonaptera (flies). A non-exhaustive list of particular genera includes, but is not limited to, *Ceratophyllus, Ctenocephalides* and *Pulex*. A non-exhaustive list of particular species includes, but is not limited to, *Ceratophyllus gallinae, Ceratophyllus niger, Ctenocephalides canis, Ctenocephalides felis* and *Pulex irritans*.

In another embodiment, a pest control composition, method and/or use disclosed herein can control a population of pests belongs to the Order Thysanoptera (thrips). A non-exhaustive list of particular genera includes, but is not limited to, *Caliothrips, Frankliniella, Heliothrips, Rhipiphorothrips, Scirtothrips Taeniothrips* and *Thrips*. A non-exhaustive list of particular species includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips*

*citri, Scirtothrips dorsalis,* and *Taeniothrips rhopalantennalis, Thrips hawaiiensis, Thrips nigropilosus, Thrips orientalis, Thrips tabaci.*

In another embodiment, a pest control composition, method and/or use disclosed herein can control a population of pests belongs to the Order Thysanura (bristletails). A non-exhaustive list of particular genera includes, but is not limited to, *Lepisma* and *Thermobia.*

In another embodiment, a pest control composition, method and/or use disclosed herein can control a population of pests belongs to the Order Acarina (mites and ticks). A non-exhaustive list of particular genera includes, but is not limited to, *Acarapsis, Acarus, Aceria, Aculops, Aculus, Amblyomma, Boophilus, Brevipalpus, Demodex, Dermacentor, Dermatophagoides, Eotetranychus, Epitrimerus, Eriophyes, Ixodes, Metatetranycus, Notoedres, Oligonychus, Panonychus, Phyllocoptruta, Polyphagotarsonemun, Rhipicephalus, Rhizoglyphus, Sarcoptes, Tegolophus, Tetranychus* and *Varroa.* A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae,* and *Varroa destructor.*

In another embodiment, a pest control composition, method and/or use disclosed herein can control a population of pests belongs to the Order Araneae (spiders). A non-exhaustive list of particular genera includes, but is not limited to, *Abracadabrella, Acacesia, Achaearanea, Actinopus, Admestina, Aganippe, Agelena, Agelenopsis, Aliatypus, Allocosa, Alopecosa, Altella, Ami, Aname, Anasaitis, Anelosimus, Anidiops, Annandaliella, Anoploscelus, Antrodiaetus, Anyphaena, Aphonopelma, Aptostichus, Araneus, Araniella, Arbanitis, Archaeodictyna, Arctosa, Argiope, Argyrodes, Ariamnes, Atrax, Attidops, Atypus, Avicularia, Bagheera, Bannana, Batesiella, Bathyphantes, Bellota, Blakistonia, Brachypelma, Bredana, Brommella, Caledothele, Callilepis, Camillina, Cantuaria, Carniella, Castianeira, Cataxia, Cavisternum, Ceratogyrus, Cerocida, Cesonia, Cethegus, Chalcoscirtus, Cheiracanthium, Cheliferoides, Chrosiothes, Chrysso, Cicurina, Citharacanthus, Clubiona, Coelotes, Colima, Coras, Craspedisia, Crossopriza, Crustulina, Cryptachaea, Cryptoparachtes, Cryptothele, Cteniza, Ctenolophus, Cubanops, Cybaeus, Cyclocosmia, Cyclosa, Cyclosternum, Cyriocosmus, Cyriopagopus, Cyrtarachne, Cyrtocarenum, Dasumia, Dictyna, Diguetia, Diplura, Dolomedes, Drassodes, Dysdera, Ebo, Encyocrates, Enoplognatha, Envia, Ephebopus, Episinus, Erigone, Eriophora, Eris, Ero, Euathlus, Eucteniza, Eucyrtops, Eumenophorus, Euoplos, Euryopis, Florinda, Galeosoma, Gasteracantha, Gea, Genysa, Ghelna, Gnaphosa, Goeldia, Gorgyrella, Grammostola, Habronattus, Habronestes, Hadites, Hadronyche, Haplopelma, Hasarius, Heligmomerus, Hentzia, Heptathela, Hersilia, Heteropoda, Heteroscodra, Hibana, Histopona, Hogna, Hoplopholcus, Hypsosinga, Hyptiotes, Hysterocrates, Icius, Idiops, Idiosoma, Inermocoelotes, Iridopelma, Kaira, Kukulcania, Larinia, Larinioides, Lasaeola, Latrodectus, Lepthyphantes, Lessertia, Leucauge, Liphistius, Lipocrea, Litoporus, Loxomphalia, Loxoptygus, Loxosceles, Lutica, Lyssomanes, Macrothele, Maevia, Mallos, Marpissa, Mascaraneus, Masteria, Mastophora, Melychiopharis, Menemerus, Messua, Metacyrba, Metaphidippus, Metellina, Metepeira, Mexigonus, Micrathena, Microhexura, Micrommata, Micropholcus, Mimetus, Misgolas, Missulena, Misumena, Misumenoides, Misumenops, Moggridgea, Moneta, Monocentropus, Myostola, Myrmekiaphila, Nanthela, Naphrys, Neoapachella, Neocteniza, Neoleptoneta, Neon, Neonella, Neoscona, Nephila, Neriene, Nihoa, Nops, Nuctenea, Nurscia, Oecobius, Olios, Oonopinus, Oonops, Opopaea, Orchestina, Ordgarius, Ornithoctonus, Ozyptila, Pachistopelma, Pachygnatha, Palfuria, Pamphobeteus, Paradamoetas, Paramarpissa, Parameta, Paraphidippus Parasteatoda, Paratropis, Pardosa, Peckhamia, Pelegrina, Pelinobius, Pellenes, Penestomus, Peucetia, Phaeacius, Philodromus, Philoponella, Phlegra, Pholcus, Phoneyusa, Phormictopus, Physocyclus, Pirata, Piratula, Pireneitega, Pisaura, Platnickina, Platycryptus, Plesiolena, Plexippus, Poecilotheria, Porrhothele, Portia, Poultonella, Predatoroonops, Prethopalpus, Prothemenops, Psalmopoeus, Psilochorus, Pterinochilus, Pyrenecosa, Rhetenor, Rugathodes, Ryuthela, Sadies, Saitis, Salticus, Sarinda, Sason, Sassacus, Scalidognathus, Schizocosa, Scoloderus, Scytodes, Segregara, Selenocosmia, Selenops, Semljicola, Seothyra, Sitticus, Smeringopus, Songthela, Sosippus, Spermophora, Spermophorides, Sphodros, Spintharus, Stanwellia, Steatoda, Stemmops, Stygopholcus, Styposis, Sybota, Synageles, Synemosyna, Synothele, Talavera, Tapinauchenius, Tartarus, Tegenaria, Tenedos, Tenuiphantes, Tetragnatha, Teyl, Thanatus, Thaumastochilus, Theraphosa, Theridion, Theridula, Thiodina, Thwaitesia, Tibellus, Tibioploides, Tidarren, Tinus, Titanidiops, Titanoeca, Tmarus, Trebacosa, Trochosa, Trogloraptor, Tychicus, Uliodon, Uloborus, Ummidia, Unicorn, Urocoras, Wabasso, Walckenaeria, Wirada, Xysticus, Zelotes, Zilla, Zodarion, Zoropsis* and *Zygoballus.*

In another embodiment, a pest control composition, method and/or use disclosed herein can control a population of pests belongs to the Order Amblypygi, Haptopoda, Opilones, Palpigradi, Phalangiotarbida, Pseudoscorpions, Ricinulei, Schizomida, Scorpions, Solifugae, Trigonotarbida, and Thelyponida.

In another embodiment, a pest control composition, method and/or use disclosed herein can control a population of pests belongs to the Order Symphyla (pseudocentipedes). A non-exhaustive list of particular genera includes, but is not limited to, *Hanseniella* and *Scutigerella.* A non-exhaustive list of particular species includes, but is not limited to, *Scutigerella immaculata.*

In another embodiment, a pest control composition, method and/or use disclosed herein can control a population of pests belongs to the *Phylum Nematoda* (round worms). A non-exhaustive list of particular genera includes, but is not limited to, *Aphelenchoides, Belonolaimus, Criconemella, Dirofilaria, Ditylenchus, Heterodera, Hirschmanniella, Hoplolaimus, Meloidogyne, Onchocerca, Pratylenchus, Radopholus* and *Rotylenchulus.* A non-exhaustive list of particular species includes, but is not limited to, *Dirofilaria immitis, Heterodera zeae, Meloidogyne incognita, Meloidogyne javanica, Onchocerca volvulus, Radopholus similis,* and *Rotylenchulus reniformis.*

Additional information regarding invertebrate pests is described in "*Handbook of Pest Control—The Behavior, Life History, and Control of Household Pests*" by Arnold Mallis, 9th Edition, copyright 2004 by GIE Media Inc., which is hereby incorporated by reference in its entirety.

The pest control compositions, method and uses described herein will most likely not harm mammals or the environment and are non-phytotoxic and can be safely applied to economically valuable plants or crops. Furthermore, the pest control compositions, method and uses described herein can be used indoors and outdoors and will not soften, dissolve, or otherwise adversely affect treated surfaces. Lastly, invertebrate pests will not build resistance to the pest control compositions, method and uses described herein.

Aspects of the present specification can also be described as follows:

1. A method of controlling a population of invertebrate pests, the method comprising, consisting essential of or consisting of applying an effective amount of a pest control composition to the population of the invertebrate pests and/or one or more locations where control of the population of the invertebrate pests is desired in a manner where the invertebrate pests will be exposed to the pest control composition, wherein application of the pest control composition results in an adverse effect on the invertebrate pests sought to be controlled, the composition comprises, consists essential of or consists of a treated, fermented microbial supernatant and one or more nonionic surfactants, wherein the composition lacks any active enzymes or live bacteria, and wherein the composition has a pH of at most 5.0.
2. Use of an effective amount of a pest control composition for controlling a population of invertebrate pests, wherein the composition comprising, consisting essential of or consisting of a treated, fermented microbial supernatant and one or more nonionic surfactants, wherein the composition lacks any active enzymes or live bacteria, and wherein the composition has a pH of at most 5.0.
3. The method according to embodiment 1 or the use according to embodiment 2, wherein the treated, fermented microbial supernatant is from a fermented yeast supernatant, a fermented bacterial supernatant, a fermented mold supernatant, or any combination thereof.
4. The method or use according to embodiment 3, wherein the fermented yeast supernatant is produced from a species of yeast belonging to the genera *Brettanomyces, Candida, Cyberlindnera, Cystofilobasidium, Debaryomyces, Dekkera, Fusarium, Geotrichum, Issatchenkia, Kazachstania, Kloeckera, Kluyveromyces, Lecanicillium, Mucor, Neurospora, Pediococcus, Penicillium, Pichia, Rhizopus, Rhodosporidium, Rhodotorula, Saccharomyces, Schizosaccharomyces, Thrichosporon, Torulaspora, Torulopsis, Verticillium, Yarrowia, Zygosaccharomyces* or *Zygotorulaspora*.
5. The method or use according to embodiment 4, wherein the fermented yeast supernatant is produced from the yeast *Saccharomyces cerevisiae*.
6. The method or use according to embodiment 3, wherein the fermented bacterial supernatant is produced from a species of bacteria belonging to the genera *Acetobacter, Arthrobacter, Aerococcus, Bacillus, Bifidobacterium, Brachybacterium, Brevibacterium, Barnobacterium, Carnobacterium, Corynebacterium, Enterococcus, Escherichia, Gluconacetobacter, Gluconobacter, Hafnia, Halomonas, Kocuria, Lactobacillus, Lactococcus, Leuconostoc, Macrococcus, Microbacterium, Micrococcus, Neisseria, Oenococcus, Pediococcus, Propionibacterium, Proteus, Pseudomonas, Psychrobacter, Salmonella, Sporolactobacillus, Staphylococcus, Streptococcus, Streptomyces, Tetragenococcus, Vagococcus, Weissells* or *Zymomonas*.
7. The method or use according to embodiment 6, wherein the fermented bacterial supernatant is produced from a species of bacteria belonging to the genus *Aspergillus*.
8. The method according to embodiments 1 or 3-7 or use according to embodiments 2-7, wherein the pest control composition comprises at least 35% by weight of the treated fermented microbial supernatant.
9. The method according to embodiments 1 or 3-8 or use according to embodiments 2-8, wherein the pest control composition comprises at most 95% by weight of the treated fermented microbial supernatant.
10. The method according to embodiments 1 or 3-9 or use according to embodiments 2-9, wherein the nonionic surfactant comprises, consists essential of or consists of a polyether nonionic surfactant, a polyhydroxyl nonionic surfactant, and/or a nonionic biosurfactant.
11. The method or use according to embodiment 10, wherein the polyhydroxyl nonionic surfactant comprises, consists essential of or consists of a sucrose ester, an ethoxylated sucrose ester, a sorbital ester, an ethoxylated sorbital ester, an alkyl glucoside, an ethoxylated alkyl glucoside, a polyglycerol ester, or an ethoxylated polyglycerol ester.
12. The method according to embodiments 1 or 3-11 or use according to embodiments 2-11, wherein the nonionic surfactant comprises, consists essential of or consists of an amine oxide, an ethoxylated alcohol, an ethoxylated aliphatic alcohol, an alkylamine, an ethoxylated alkylamine, an ethoxylated alkyl phenol, an alkyl polysaccharide, an ethoxylated alkyl polysaccharide, an ethoxylated fatty acid, an ethoxylated fatty alcohol, or an ethoxylated fatty amine, or a nonionic surfactant having the general formula of $H(OCH_2CH_2)_xOC_6H_4R^1$, $(OCH_2CH_2)_xOR^2$, or $H(OCH_2CH_2)_xOC(O)R^2$, wherein x represents the number of moles of ethylene oxide added to an alkyl phenol and/or a fatty alcohol or a fatty acid, $R^1$ represents a long chain alkyl group and, $R^2$ represents a long chain aliphatic group.
13. The method or use according to embodiment 12, wherein $R^1$ is a $C_7$-$C_{10}$ normal-alkyl group and/or wherein $R^2$ is a $C_{12}$-$C_{20}$ aliphatic group.
14. The method according to embodiments 1 or 3-13 or use according to embodiments 2-13, wherein the nonionic surfactant is an ethoxylated nonyl phenol, an ethoxylated octyl phenol, an ethoxylated ceto-oleyl alcohol, an ethoxylated ceto-stearyl alcohol, an ethoxylated decyl alcohol, an ethoxylated dodecyl alcohol, an ethoxylated tridecyl alcohol, or an ethoxylated castor oil.
15. The method according to embodiments 1 or 3-14 or use according to embodiments 2-14, wherein the pest control composition comprises from about 1% to about 15% by weight of the one or more nonionic surfactants.
16. The method or use according to embodiment 15, wherein the pest control composition comprises from about 5% to about 13% by weight of the one or more nonionic surfactants.
17. The method or use according to embodiment 16, wherein the pest control composition comprises from about 7% to about 11% by weight of the one or more nonionic surfactants.
18. The method according to embodiments 1 or 3-17 or use according to embodiments 2-17, wherein the pest control composition further comprises, consists essential of or consists of one or more anionic surfactants.
19. The method or use according to embodiment 18, wherein the pest control composition comprises from about 0.5% to about 10% by weight of the one or more anionic surfactants.

20. The method or use according to embodiment 19, wherein the pest control composition comprises from about 1% to about 8% by weight of the one or more anionic surfactants.
21. The method or use according to embodiment 19, wherein the pest control composition comprises from about 2% to about 6% by weight of the one or more anionic surfactants.
22. The method according to embodiments 1 or 3-21 or use according to embodiments 2-21, wherein the pH is at most 4.5.
23. The method or use according to embodiment 22, wherein the pH about 3.7 to about 4.2.
24. The method according to embodiments 1 or 3-23 or use according to embodiments 2-23, wherein the pest control composition further comprises an antimicrobial.
25. The method according to embodiments 1 or 3-24 or use according to embodiments 2-24, wherein the pest control composition further comprises an abrasive agent.
26. The method according to embodiments 1 or 3-25 or use according to embodiments 2-25, wherein the pest control composition further comprises a plant essential oil.
27. The method according to embodiments 1 or 3-26 or use according to embodiments 2-26, wherein application of the pest control composition causes an adverse effect on the population of the invertebrate pests sought to be controlled.
28. The method according to embodiments 1 or 3-27 or use according to embodiments 2-27, wherein the effective amount of the pest control composition results in an adverse effect to the invertebrate pests sought to be controlled.
29. The method or use according to embodiment 28, wherein the effective amount of the pest control composition adversely effects about 70%, about 75%, about 80%, about 85%, about 86%, about 87%, about 88%, about 89%, about 90%, about 91%, about 92%, about 93%, about 94%, about 95%, about 96%, about 97%, about 98% or about 99%; or at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%; or at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99%; or about 70% to about 80%, about 70% to about 85%, about 70% to about 90%, about 70% to about 95%, about 70% to about 99%, about 75% to about 85%, about 75% to about 90%, about 75% to about 95%, about 75% to about 99%, about 80% to about 90%, about 80% to about 95%, about 80% to about 99%, about 85% to about 93%, about 85% to about 95%, about 85% to about 97%, about 85% to about 99%, about 90% to about 93%, about 90% to about 95%, about 90% to about 97%, about 90% to about 99%, about 93% to about 95%, about 93% to about 97%, about 93% to about 99%, about 95% to about 97% or about 95% to about 99% of the invertebrate pests sought to be controlled.
30. The method according to embodiments 1 or 3-29 or use according to embodiments 2-29, wherein the effective amount of the pest control composition results in mortality of the invertebrate pests sought to be controlled.
31. The method or use according to embodiment 30, wherein the effective amount of the pest control composition results in mortality of about 70%, about 75%, about 80%, about 85%, about 86%, about 87%, about 88%, about 89%, about 90%, about 91%, about 92%, about 93%, about 94%, about 95%, about 96%, about 97%, about 98% or about 99%; or at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%; or at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99%; or about 70% to about 80%, about 70% to about 85%, about 70% to about 90%, about 70% to about 95%, about 70% to about 99%, about 75% to about 85%, about 75% to about 90%, about 75% to about 95%, about 75% to about 99%, about 80% to about 90%, about 80% to about 95%, about 80% to about 99%, about 85% to about 93%, about 85% to about 95%, about 85% to about 97%, about 85% to about 99%, about 90% to about 93%, about 90% to about 95%, about 90% to about 97%, about 90% to about 99%, about 93% to about 95%, about 93% to about 97%, about 93% to about 99%, about 95% to about 97% or about 95% to about 99% of the invertebrate pests sought to be controlled.
32. The method according to embodiments 1 or 3-31 or use according to embodiments 2-31, wherein the effective amount of the pest control composition reduces the size of a population of the invertebrate pests sought to be controlled.
33. The method or use according to embodiment 32, wherein the effective amount of the pest control composition reduce the size of a population of the invertebrate pests sought to be controlled by about 70%, about 75%, about 80%, about 85%, about 86%, about 87%, about 88%, about 89%, about 90%, about 91%, about 92%, about 93%, about 94%, about 95%, about 96%, about 97%, about 98% or about 99%; or at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%; or at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99%; or about 70% to about 80%, about 70% to about 85%, about 70% to about 90%, about 70% to about 95%, about 70% to about 99%, about 75% to about 85%, about 75% to about 90%, about 75% to about 95%, about 75% to about 99%, about 80% to about 90%, about 80% to about 95%, about 80% to about 99%, about 85% to about 93%, about 85% to about 95%, about 85% to about 97%, about 85% to about 99%, about 90% to about 93%, about 90% to about 95%, about 90% to about 97%, about 90% to about 99%, about 93% to about 95%, about 93% to about 97%, about 93% to about 99%, about 95% to about 97% or about 95% to about 99%.

34. The method according to embodiments 1 or 3-33 or use according to embodiments 2-33, wherein the effective amount of the pest control composition deters a population of the invertebrate pests sought to be controlled from entering or infesting one or more locations.

35. The method or use according to embodiment 34, wherein the effective amount of the pest control composition deters about 70%, about 75%, about 80%, about 85%, about 86%, about 87%, about 88%, about 89%, about 90%, about 91%, about 92%, about 93%, about 94%, about 95%, about 96%, about 97%, about 98% or about 99%; or at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99%; or at most 70%, at most 75%, at most 80%, at most 85%, at most 86%, at most 87%, at most 88%, at most 89%, at most 90%, at most 91%, at most 92%, at most 93%, at most 94%, at most 95%, at most 96%, at most 97%, at most 98% or at most 99%; or about 70% to about 80%, about 70% to about 85%, about 70% to about 90%, about 70% to about 95%, about 70% to about 99%, about 75% to about 85%, about 75% to about 90%, about 75% to about 95%, about 75% to about 99%, about 80% to about 90%, about 80% to about 95%, about 80% to about 99%, about 85% to about 90%, about 85% to about 95%, about 85% to about 97%, about 85% to about 99%, about 90% to about 95%, about 90% to about 97%, about 90% to about 99%, about 93% to about 95%, about 93% to about 97%, about 93% to about 99%, about 95% to about 97% or about 95% to about 99% of a population of the invertebrate pests from entering or infesting one or more locations.

36. The method or use according to embodiment 27, wherein application of the pest control composition causes at least 10% mortality of the invertebrate pests in the population, causes at least 10% reduction in the size of the population of the invertebrate pests sought to be controlled, and/or deters at least 10% of the invertebrate pests in the population from entering or infesting the one or more locations.

37. The method according to embodiments 1 or 3-36 or use according to embodiments 2-36, wherein the invertebrate pests comprise an arthropod or a nematode.

38. The method or use according to embodiment 37, wherein the invertebrate pests includes round worms, cockroaches, ants, flies, spiders, mites, aphids, thrips, whiteflies, loopers, worms, beetles, leafrollers, moths or weevils.

39. The method or use according to embodiment 37, wherein the arthropod comprises an insect, an arachnid, or a pseudocentipede.

40. The method or use according to embodiment 39, wherein the insect is an Anopluran, a Coleopteran, a Dermapteran, a Dictyopteran, a Dipteran, a Hemipteran, a Homopteran, a Hymenopteran, an Isopteran, a Lepidopteran, a Mallophagan, an Orthopteran, a Phthirapteran, a Siphonapteran, a Thysanopteran or a Thysanuran.

41. The method or use according to embodiment 39, wherein the arachnid is an Acarina, an Araneae, an Amblypygi, a Haptopoda, an Opilone, a Palpigradi, a Phalangiotarbida, a Pseudoscorpions, a Ricinulei, a Schizomida, a Scorpion, a Solifugae, a Trigonotarbida or a Thelyponida.

42. The method according to embodiments 1 or 3-41 or use according to embodiments 2-41, wherein the invertebrate pest includes members in the egg, larval, nymphal, juvenile, pupal, and adult stage of development.

43. The method according to embodiments 1 or 3-42 or use according to embodiments 2-42, wherein the one or more locations comprises a plant or group of plants or part of a plant, a particular area of land, or a man-made structure.

44. The method or use according to embodiment 43, wherein the particular area of land is a lawn, a garden, a nursery or an agricultural field.

45. The method or use according to embodiment 43, wherein the man-made structure is a commercial building, a residential house, a community facility, a barn, a stable, a shed, a greenhouse or any other physical structure.

46. The method according to embodiments 1 or 3-45 or use according to embodiments 2-45, wherein the pest control composition is substantially non-toxic to humans, mammals, plants and the environment.

47. The method according to embodiments 1 or 3-46 or use according to embodiments 2-46, wherein the pest control composition is biodegradable.

48. A pest control composition comprising, consisting essential of or consisting of a treated, fermented microbial supernatant and one or more nonionic surfactants, wherein the composition lacks any active enzymes or live bacteria, and wherein the composition has a pH below 5.0.

49. The pest control composition according to embodiment 48, wherein the treated, fermented microbial supernatant is from a fermented yeast supernatant, a fermented bacterial supernatant, a fermented mold supernatant, or any combination thereof.

50. The pest control composition according to embodiment 49, wherein the fermented yeast supernatant is produced from a species of yeast belonging to the genera *Brettanomyces, Candida, Cyberlindnera, Cystofilobasidium, Debaryomyces, Dekkera, Fusarium, Geotrichum, Issatchenkia, Kazachstania, Kloeckera, Kluyveromyces, Lecanicillium, Mucor, Neurospora, Pediococcus, Penicillium, Pichia, Rhizopus, Rhodosporidium, Rhodotorula, Saccharomyces, Schizosaccharomyces, Thrichosporon, Torulaspora, Torulopsis, Verticillium, Yarrowia, Zygosaccharomyces* or *Zygotorulaspora.*

51. The pest control composition according to embodiment 50, wherein the fermented yeast supernatant is produced from the yeast *Saccharomyces cerevisiae.*

52. The pest control composition according to embodiment 49, wherein the fermented bacterial supernatant is produced from a species of bacteria belonging to the genera *Acetobacter, Arthrobacter, Aerococcus, Bacillus, Bifidobacterium, Brachybacterium, Brevibacterium, Barnobacterium, Carnobacterium, Corynebacterium, Enterococcus, Escherichia, Gluconacetobacter, Gluconobacter, Hafnia, Halomonas, Kocuria, Lactobacillus, Lactococcus, Leuconostoc, Macrococcus, Microbacterium, Micrococcus, Neisseria, Oenococcus, Pediococcus, Propionibacterium, Proteus, Pseudomonas, Psychrobacter, Salmonella, Sporolactobacillus,*

*Staphylococcus, Streptococcus, Streptomyces, Tetragenococcus, Vagococcus, Weissells* or *Zymomonas*.

53. The pest control composition according to embodiment 52, wherein the fermented bacterial supernatant is produced from a species of bacteria belonging to the genus *Aspergillus*.
54. The pest control composition according to any one of embodiments 48-53, wherein the pest control composition comprises at least 35% by weight of the treated fermented microbial supernatant.
55. The pest control composition according to any one of embodiments 48-54, wherein the pest control composition comprises at most 95% by weight of the treated fermented microbial supernatant.
56. The pest control composition according to any one of embodiments 48-55, wherein the nonionic surfactant comprises, consists essential of or consists of a polyether nonionic surfactant, a polyhydroxyl nonionic surfactant, and/or a biosurfactant.
57. The pest control composition according to embodiment 56, wherein the polyhydroxyl nonionic surfactant comprises, consists essential of or consists of a sucrose ester, an ethoxylated sucrose ester, a sorbital ester, an ethoxylated sorbital ester, an alkyl glucoside, an ethoxylated alkyl glucoside, a polyglycerol ester, or an ethoxylated polyglycerol ester.
58. The pest control composition according to any one of embodiments 48-57, wherein the nonionic surfactant comprises, consists essential of or consists of an amine oxide, an ethoxylated alcohol, an ethoxylated aliphatic alcohol, an alkylamine, an ethoxylated alkylamine, an ethoxylated alkyl phenol, an alkyl polysaccharide, an ethoxylated alkyl polysaccharide, an ethoxylated fatty acid, an ethoxylated fatty alcohol, or an ethoxylated fatty amine, or a nonionic surfactant having the general formula of $H(OCH_2CH_2)_xOC_6H_4R^1$, $(OCH_2CH_2)_xOR^2$, or $H(OCH_2CH_2)_xOC(O)R^2$, wherein x represents the number of moles of ethylene oxide added to an alkyl phenol and/or a fatty alcohol or a fatty acid, $R^1$ represents a long chain alkyl group and, $R^2$ represents a long chain aliphatic group.
59. The pest control composition according to embodiment 58, wherein $R^1$ is a $C_7$-$C_{10}$ normal-alkyl group and/or wherein $R^2$ is a $C_{12}$-$C_{20}$ aliphatic group.
60. The pest control composition according to any one of embodiments 48-59, wherein the nonionic surfactant is an ethoxylated nonyl phenol, an ethoxylated octyl phenol, an ethoxylated ceto-oleyl alcohol, an ethoxylated ceto-stearyl alcohol, an ethoxylated decyl alcohol, an ethoxylated dodecyl alcohol, an ethoxylated tridecyl alcohol, or an ethoxylated castor oil.
61. The pest control composition according to any one of embodiments 48-60, wherein the pest control composition comprises from about 1% to about 15% by weight of the one or more nonionic surfactants.
62. The pest control composition according to embodiment 60, wherein the pest control composition comprises from about 5% to about 13% by weight of the one or more nonionic surfactants.
63. The pest control composition according to embodiment 61, wherein the pest control composition comprises from about 7% to about 11% by weight of the one or more nonionic surfactants.
64. The pest control composition according to any one of embodiments 48-63, wherein the pest control composition further comprises, consists essential of or consists of one or more anionic surfactants.
65. The pest control composition according to embodiment 64, wherein the pest control composition comprises from about 0.5% to about 10% by weight of the one or more anionic surfactants.
66. The pest control composition according to embodiment 65, wherein the pest control composition comprises from about 1% to about 8% by weight of the one or more anionic surfactants.
67. The pest control composition according to embodiment 66, wherein the pest control composition comprises from about 2% to about 6% by weight of the one or more anionic surfactants.
68. The pest control composition according to any one of embodiments 48-67, wherein the pH is at most 4.5.
69. The pest control composition according to embodiment 88, wherein the pH about 3.7 to about 4.2.
70. The pest control composition according to embodiments 48-69, wherein the pest control composition further comprises an antimicrobial.
71. The pest control composition according to embodiments 48-70, wherein the pest control composition further comprises an abrasive agent.
72. The pest control composition according to embodiments 48-71, wherein the pest control composition further comprises a plant essential oil.
73. The pest control composition according to any one of embodiments 48-72, wherein the pest control composition is substantially non-toxic to humans, mammals, plants and the environment.
74. The pest control composition according to any one of embodiments 48-73, wherein the pest control composition is biodegradable.
75. A method of controlling a population of invertebrate pests, the method comprising, consisting essential of or consisting of applying an effective amount of a pest control composition as defined in any one of embodiments 48-74 to the population of the invertebrate pests and/or one or more locations where control of the population of the invertebrate pests is desired in a manner where the invertebrate pests will be exposed to the pest control composition, wherein application of the pest control composition results in an adverse effect on the invertebrate pests sought to be controlled.
76. Use of an effective amount of a pest control composition as defined in any one of embodiments 48-74 for controlling a population of invertebrate pests.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the pest control compositions, or methods or uses of controlling a pest population disclosed herein.

Example 1

Preparation of Treated Fermented Yeast Supernatant 1

To prepare a treated fermented yeast supernatant, a fermentation reaction is set up in which about 1,000 L of warm water having a temperature of between about 29° C. to about 38° C. was placed in a large jacketed mixing kettle. To the water was added about 84.9 kg black untreated cane molasses, about 25.2 kg raw cane sugar and about 1.2 kg magnesium sulfate. The mixture was thoroughly blended, after which about 11.4 kg diastatic malt and about 1.2 kg baker's yeast were added and agitated slightly. The mixture is incubated at about 26° C. to about 42° C. for about 3 days, after which the effervescent reaction had subsided, indicating essentially complete fermentation. At the end of the fermentation the yeast fermentation composition is centrifuged to remove the "sludge" formed during the fermentation. The resulting fermentation supernatant (about 98.59%, by weight) was collected and sterilized by autoclaving. The treated fermented yeast supernatant can then be stored in liquid form for subsequent use. Alternatively, the treated fermented yeast supernatant can be spray dried by methods known in the art to produce a dry powder. The dry powder form can also be stored for subsequent use.

Example 2

Preparation of Treated Fermented Yeast Supernatant 2

To prepare a treated fermented yeast supernatant, a fermentation reaction is set up in which about 1,000 L of warm water having a temperature of between about 29° C. to about 38° C. was placed in a large jacketed mixing kettle. To the water was added about 42.5 kg black untreated cane molasses, about 12.6 kg raw cane sugar and about 1.2 kg magnesium sulfate. The mixture was thoroughly blended, after which about 10.3 kg diastatic malt and about 1.2 kg baker's yeast were added and agitated slightly. The mixture is incubated at about 26° C. to about 42° C. for about 3 days, after which the effervescent reaction had subsided, indicating essentially complete fermentation. At the end of the fermentation the yeast fermentation culture is centrifuged to remove the "sludge" formed during the fermentation. The resulting fermentation yeast supernatant (about 98.59%, by weight) was collected and treated by autoclaving. The treated fermented yeast supernatant can then be stored in liquid form for subsequent use. Alternatively, the treated fermented yeast supernatant can be spray dried by methods known in the art to produce a dry powder. The dry powder form can also be stored for subsequent use.

Example 3

Preparation of Treated Fermented Yeast Supernatant 3

To prepare a treated fermented yeast supernatant, a fermentation reaction is set up in which about 1,000 L of warm water having a temperature of between about 29° C. to about 38° C. was placed in a large jacketed mixing kettle. To the water was added about 21.3 kg black untreated cane molasses, about 6.3 kg raw cane sugar and about 1.2 kg magnesium sulfate. The mixture was thoroughly blended, after which about 9.3 kg diastatic malt and about 1.2 kg baker's yeast were added and agitated slightly. The mixture is incubated at about 26° C. to about 42° C. for about 3 days, after which the effervescent reaction had subsided, indicating essentially complete fermentation. At the end of the fermentation the yeast fermentation culture is centrifuged to remove the "sludge" formed during the fermentation. The resulting fermentation supernatant (about 98.59%, by weight) was collected and treated by autoclaving. The treated fermented yeast supernatant can then be stored in liquid form for subsequent use. Alternatively, the treated fermented yeast supernatant can be spray dried by methods known in the art to produce a dry powder. The dry powder form can also be stored for subsequent use.

Example 4

Preparation of Pest Control Composition

To prepare a pest control composition, 1,000 L of hot sterile water (about 60° C. to about 65° C.) was added to 1,000 L of treated fermented yeast supernatant in a large jacketed mixing kettle. To this mixture was added about 168.8 kg of TERGITOL™ 15-S-7, a linear secondary alcohol ethoxylate, about 168.8 kg of TERGITOL™ 15-S-5, a linear secondary alcohol ethoxylate, about 67.5 kg of DOWFAX™ 2A1, alkyldiphenyloxide disulfonate, and about 67.5 kg of TRITON™ H-66, phosphate polyether ester. This mixture was thoroughly blended to effect solution. Water was then added to bring the volume to about 4,500 L and stirred until complete mixing had been obtained. The pH of the resulting pest control composition was adjusted to from about 3.7 to about 4.2 with phosphoric acid. The pH adjusted pest control composition was then filter sterilized to remove any microbial contamination.

The composition was found to be nonirritating to skin tissue, nontoxic and could be stored in a cool location over periods of months without any discernible loss in effectiveness or deterioration.

DOWFAX™ 2A1 can be substituted with an anionic biosurfactant such as, e.g., STEPONOL® AM 30-KE, an ammonium lauryl sulfate, STEPONOL® EHS, a sodium 2-ethyl hexyl sulfate, or a combination thereof.

Optionally, the resulting pest control composition may then be mixed with preservative or stabilizing agents, such as about 1% by weight sodium benzoate, about 0.01% by weight imidazolidinyl urea, about 0.15% by weight diazolidinyl urea, about 0.25% by weight calcium chloride. With continuous agitation, sodium benzoate, imidazolidinyl urea, diazolidinyl urea and calcium chloride are added. The temperature of the mixture is then slowly raised to about 40° C. and the mixture is agitated continuously. The temperature is maintained at about 40° C. for about one hour to ensure that all the components of the mixture are dissolved. The mixture is then cooled to from about 20° C. to about 25° C. The pH of the resulting pest control composition was adjusted to from about 3.7 to about 4.2 with phosphoric acid. The pH adjusted pest control composition was then filter sterilized to remove any microbial contamination.

Example 5

Preparation of Pest Control Composition

To prepare a pest control composition, 850 L of hot sterile water (about 60° C. to about 65° C.) was placed in a large jacketed mixing kettle. To the water was added about 7.62 g treated fermented yeast supernatant dried powder, about 37.5 kg of TERGITOL™ 15-S-7, a linear secondary alcohol ethoxylate, about 37.5 kg of TERGITOL™ 15-S-5, a linear secondary alcohol ethoxylate, about 15.0 kg of DOWFAX™ 2A1, alkyldiphenyloxide disulfonate, and about 25.0 kg of TRITON™ H-66, phosphate polyether ester. This mixture was thoroughly blended to effect solution. Water was then added to bring the volume to about 1,000 L and stirred until complete mixing had been obtained. The pH of the resulting pest control composition was adjusted to from about 3.7 to about 4.2 with phosphoric acid. The pH adjusted pest control composition was then filter sterilized to remove any microbial contamination.

Optionally, the resulting pest control composition may then be mixed with preservative or stabilizing agents, such as about 1% by weight sodium benzoate, about 0.01% by weight imidazolidinyl urea, about 0.15% by weight diazolidinyl urea, about 0.25% by weight calcium chloride. With continuous agitation, sodium benzoate, imidazolidinyl urea, diazolidinyl urea and calcium chloride are added. The temperature of the mixture is then slowly raised to about 40° C. and the mixture is agitated continuously. The temperature is maintained at about 40° C. for about one hour to ensure that all the components of the mixture are dissolved. The mixture is then cooled to from about 20° C. to about 25° C. The pH of the resulting pest control composition was adjusted to from about 3.7 to about 4.2 with phosphoric acid. The pH adjusted pest control composition was then filter sterilized to remove any microbial contamination.

The composition was found to be nonirritating to skin tissue, nontoxic and could be stored in a cool location over periods of months without any discernible loss in effectiveness or deterioration.

DOWFAX™ 2A1 can be substituted with an anionic biosurfactant such as, e.g., STEPONOL® AM 30-KE, an ammonium lauryl sulfate, STEPONOL® EHS, a sodium 2-ethyl hexyl sulfate, or a combination thereof.

As an alternative to the treated fermented yeast supernatant dried powder disclosed in Examples 1-3, commercially available treated fermented yeast supernatant dried powders can be used, including, e.g., TASTONE® 154, TASTONE® 210 or TASTONE® 900.

Example 6

Pest Control Experiment

In this example, a pest control composition disclosed herein was tested for its ability to control a various pest infestation.

Approximately 100 cochroches were placed in a stainless steel bin. A 1:100 dilution of a pest control composition disclosed herein was applied to the insects using a spray bottle. All cochroches were killed within about 10 to about 15 minutes of pest control composition application.

Ants treated in a residential structure using a pest control composition disclosed. A 1:50 dilution of a pest control composition disclosed herein was applied to a location were the ants were present using a spray bottle. All ants were killed within about 10 to about 15 minutes of pest control composition application.

Fire ants treated in a field using a pest control composition disclosed. A 1:50 dilution of a pest control composition disclosed herein was applied to a location were the fire ants were present using a spray bottle. All fire ants were killed within about 10 to about 15 minutes of pest control composition application.

Dogs infested with fleas were treated with a pest control composition disclosed herein. A 1:100 dilution of a pest control composition disclosed herein was applied to a location were the fleas were present using a spray bottle. All fleas were killed within about 5 to about 10 minutes of pest control composition application.

Plants infected with white flies treated with a pest control composition disclosed herein. Three groups of white flies infested plants were treated with either a 1:1000 dilution, 1:2000 dilution or 1:2500 dilution of a pest control composition disclosed herein. Application was in a location were the white flies were present by using a spray bottle. All white flies were killed within about 2 to about 5 minutes of pest control composition application from any dilution.

Flowering plants infected with aphids treated with a pest control composition disclosed herein. Three groups of aphid infested plants were treated with either a 1:1000 dilution, 1:2000 dilution or 1:2500 dilution of a pest control composition disclosed herein. Application was in a location were the aphids were present by using a spray bottle. All aphids were killed within about 2 to about 5 minutes of pest control composition application from any dilution.

Beetles treated in a field using a pest control composition disclosed. A 1:100 dilution of a pest control composition disclosed herein was applied to a location were the beetles were present using a spray bottle. All beetles were killed within about 10 to about 15 minutes of pest control composition application.

Dogs infested with fleas were treated with a pest control composition disclosed herein. A 1:100 dilution of a pest control composition disclosed herein was applied to a location were the fleas were present using a spray bottle. All fleas were killed within about 5 to about 10 minutes of pest control composition application.

Compost piles infested with fly larvae were treated with a pest control composition disclosed herein. A 1:100 dilution of a pest control composition disclosed herein was applied to the insects using a spray bottle. All fly larvae were killed within about 2 to about 5 minutes of pest control composition application.

Plants infested with mites ere treated with a pest control composition disclosed herein. Three groups of mite infested plants were treated with either a 1:1000 dilution, 1:2000 dilution or 1:2500 dilution of a pest control composition disclosed herein. Application was in a location were the mites were present by using a spray bottle. All mites were killed within about 2 to about 5 minutes of pest control composition application from any dilution.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method of controlling a population of invertebrate pests, the method comprising applying an effective amount of a pest control composition to the population of the invertebrate pests and/or one or more locations where control of the population of the invertebrate pests is desired, the composition comprising a treated, fermented yeast supernatant including bio-nutrients, minerals and amino acids, and about 1% to about 15% by weight of one or more nonionic surfactants,
wherein application of the composition creates microbubbles that increase oxygen dispersion resulting in higher dissolved oxygen levels and accelerate molecular interactions that mediate cleavage of chemical bonds,
wherein the treated, fermented yeast supernatant lacks any active enzymes, activatable pro-enzymes, or any enzymatic activity,
wherein the composition lacks any active enzymes, activatable pro-enzymes, or any enzymatic activity, and
wherein the composition has a pH below 5.0.

2. The method according to claim 1, wherein the pest control composition comprises at least 35% by weight of the treated fermented yeast supernatant.

3. The method according to claim 1, wherein the pest control composition comprises at most 95% by weight of the treated fermented yeast supernatant.

4. The method according to claim 1, wherein the pest control composition comprises at least 3.0% by weight of the one or more nonionic surfactants.

5. The method according to claim 4, wherein the pest control composition comprises from about 5% to about 13% by weight of the one or more nonionic surfactants.

6. The method according to claim 5, wherein the pest control composition comprises from about 7% to about 11% by weight of the one or more nonionic surfactants.

7. The method according to claim 1, wherein the pest control composition further comprises one or more anionic surfactants.

8. The method according to claim 7, wherein the pest control composition comprises from about 0.5% to about 10% by weight of the one or more anionic surfactants.

9. The method according to claim 8, wherein the pest control composition comprises from about 1% to about 8% by weight of the one or more anionic surfactants.

10. The method according to claim 9, wherein the pest control composition comprises from about 2% to about 6% by weight of the one or more anionic surfactants.

11. The method according to claim 1, wherein the pH is at most 4.5.

12. The method according to claim 1, wherein application of the pest control composition causes an adverse effect on the population of the invertebrate pests sought to be controlled.

13. The method according to claim 12, wherein application of the pest control composition causes at least 10% mortality of the invertebrate pests in the population, causes at least 10% reduction in the size of the population of the invertebrate pests sought to be controlled, and/or deters at least 10% of the invertebrate pests in the population from entering or infesting the one or more locations.

14. The method according to claim 1, wherein the invertebrate pests comprise an insect, an arachnid or a nematode.

15. The method according to claim 14, wherein the invertebrate pest includes members in the egg, larval, nymphal, juvenile, pupal, and adult stage of development.

16. The method according to claim 1, wherein the one or more locations comprises a plant or group of plants or part of a plant, a particular area of land, or a man-made structure.

17. The method according to claim 16, wherein the particular area of land is a lawn, a garden, a nursery or an agricultural field.

18. The method according to claim 16, wherein the man-made structure is a commercial building, a residential house, a community facility, a barn, a stable, a shed, a greenhouse or any other physical structure.

19. The method according to claim 1, wherein the pest control composition is biodegradable.

* * * * *